US005767152A

United States Patent [19]

Nielsen et al.

[11] Patent Number: 5,767,152
[45] Date of Patent: Jun. 16, 1998

[54] COMPOSITION AND METHODS FOR STIMULATING HAIR GROWTH

[76] Inventors: Thor Bagger Nielsen, 5302 Crestedge La., Rockville, Md. 20853; Liying Sun, 854 Quince Orchard Blvd. 102, Gaithersburg, Md. 20878

[21] Appl. No.: 434,994

[22] Filed: May 4, 1995

[51] Int. Cl.$^6$ ............................................. A61K 31/275
[52] U.S. Cl. .................................................. 514/526
[58] Field of Search ....................................... 514/526

[56] References Cited

U.S. PATENT DOCUMENTS

| | | |
|---|---|---|
| 4,596,812 | 6/1986 | Chidsey . |
| 4,814,351 | 3/1989 | Mathews . |
| 4,866,038 | 9/1989 | Hruby . |
| 4,874,791 | 10/1989 | Adachi et al. . |
| 4,918,055 | 4/1990 | Hruby et al. . |
| 4,937,232 | 6/1990 | Bell et al. . |
| 4,978,681 | 12/1990 | Adachi et al. . |
| 5,026,691 | 6/1991 | Kligman . |
| 5,049,547 | 9/1991 | Hruby et al. . |
| 5,053,410 | 10/1991 | Grollier . |
| 5,055,456 | 10/1991 | Harris . |
| 5,096,697 | 3/1992 | Adachi . |
| 5,124,354 | 6/1992 | Green . |
| 5,157,036 | 10/1992 | Grollier . |
| 5,158,955 | 10/1992 | Gibson . |
| 5,185,325 | 2/1993 | Brawn . |
| 5,229,271 | 7/1993 | Philpott . |
| 5,326,690 | 7/1994 | Xu et al. . |

OTHER PUBLICATIONS

Daniel B. Rifkin et al., "TGF-β:Structure, Function, and Formation," *Thromb. Haemost.* 70:177–179 (1993).

Harold L. Moses et al., "TGF-B Stimulation and Inhibition of Cell Proliferation: New Mechanistic Insights," *Cell* 63:245–247 (1990).

"Nexband Liquid" by Veterinary Products Laboratories, Phoenix, Arizona, an undated product insert from a product purchased in 1995.

A. Reiter, "Sarkomerzeugende Wirkung des Gewebeklebers Histoacryl–blau an der Ratts," Z. exp. Chir. Transplant. kunstl., 20, pp. 55–59 (1987) [Butyl–2–cyanoacrylate (Histoacryl–blue) was implanted in 11 cases of sarcomas developed at the site of implantation.]

A.G. Messenger, "The Control of Hair Growth: An Overview," J. Investig. Dermatol., 101, 4S–9S (1993).

S. Arase, et al., "Co-culture of human Hair Follicles and Dermal Papillae in a Collagen Matrix," J. of Dermatol., 17, pp. 667–676 (1990).

A.B. Roberts and M. B. Sporn, "Physiological Actions & Clinical Applications of Transforming Growth Factor–B (TGF–B)," Growth Factors, 8, pp. 1–9 (1993).

A.B. Roberts, et al., "Transforming Growth Factor–B: Multifunctional Regulator of Differentiation and Development," Phil. Trans. R. Soc. Lond., B 327, pp. 145–154 (1990).

A.E. Buhl, et al., "Minoxidil Sulfate is the Active Metabolite that Stimulates Hair Follicles," J. Investig. Dermatol., 95, pp. 553–557 (1990).

R.S. Rittmaster, "Topical Anti-Androgens in the Treatment of Male-Pattern Baldness," Clinics in Dermatology, 6, pp. 122–128 (1988).

D.M. Kingsley, "The TGF–B Superfamily: New Members, New Receptors, and New Genetic Tests of Function in Different Organisms," Genes & Development, 8, pp. 133–146 (1994).

D.L. du Cros, "Fibroblast Growth Factor and Epidermal Growth Factor in Hair Development," J. Investig. Dermatol., 101S, pp. 108S–113S (1993).

D.L. du Cros, "Fibroblast Growth Factor Influences the Development and Cycling of Murine Hair Follicles," Developmental Biology, 156, pp. 444–453 (1993).

K. Sellheyer, et al., "Inhibition of Skin Development by Overexpression of Transforming Growth Factor B1 in the Epidermis of Transgenic Mice," Proc. Natl. Acad. Sci., 90, pp. 5237–5241 (1993).

G.F. Pierce, et al., "Stimulation of All Epithelial Elements during Skin Regeneration by Keratinocyte Growth Factor," J. Exp. Med., 179, pp. 831–830 (1994).

A. Gilhar, et al., "Hair Growth in Human Split Thickness skin Grafts Transplanted, onto Nude Rats: The Role of Cyclosporin," Dermatologica, 181, pp. 117–121 (1990).

A. Gilhar, et al., "Topical Cyclosporin Induces Hair Growth in Human Split Skin Grafted onto Nude Mice," Acta Derm. Venereol. (Stockh.), 71, pp. 327–330 (1991).

J.D. Harwick, et al., "Review of Cyanoacrylate Tissue Glues with Emphasis on Their Otorhinolaryngological Applications," Laryngoscope, 94, 210–213 (1984).

J. Massague, "The Transforming Growth Factor–B Family," Annu. Rev. Cell Biol., 6, pp. 597–641 (1990).

J.R. Spindler & J.L. Data, "Female Androgenetic Alopecia a Review," Dermatology Nursing, 4, pp. 93–99 (1992).

A.K.C. Leung & W.L.M> Robson, "Hair Loss in Children," J. Roy Soc. Health, Oct. 1993, pp. 252–256 (1993).

M.E. Sawaya, "Biochemical Mechanisms Regulating Human Hair Growth," Skin Pharmacol., 7, pp. 5–7 (1994).

M.E. Hardy, "The Secret Life of the Hair Follicle," Trends in Genetics, 8, pp. 55–61 (1992).

J.M. Holland, "Animal Models of Alopecia," Clinics in Dermatology, 6, pp. 159–162 (1988).

M. Reiss & A.C. Sartorelli, "Regulation of Growth and Differentiation of Human Keratinocytes by Type B Transforming Growth Factor," Cancer Research, 47, pp. 6705–6709 (1987).

(List continued on next page.)

*Primary Examiner*—Rebecca Cook
*Attorney, Agent, or Firm*—Fleshner & McConathy PLLC

[57] ABSTRACT

A method for regulation of hair growth in an adult mammal, in which a trichogenic composition is applied to the skin. Also disclosed are methods for inducing skin differentiation and stimulating hair growth, wherein a formulation of a trichogenic composition is applied to the skin.

25 Claims, 28 Drawing Sheets
(10 of 28 Drawing(s) in Color)

OTHER PUBLICATIONS

J.N. Mansbridge & P.C. Hanawalt, "Role of Transforming Growth Factor B in the Maturation of Human Epidermal Keratinocytes," J. Investig. Dermatol., 90, pp. 336–341 (1988).

A.F. Hood, "Cutaneous Side Effects of Cancer Chemotherapy," Medical Clinics of N. America, 70, pp. 187–209 (1986).

B.W. Cline, "Prevention of Chemotherapy–Induced Alopecia: A Review of the Literature," Cancer Nursing, 7, pp. 221–228 (1984).

R.P.R. Dawber, "Aetiology and Pathophysiology of Hair Loss," Dermatologica, 175, pp. 23–28 (1987).

W.C. Weinberg, et al., "Reconstitution of Hair Follicle in vivo: Determination of Follicle Formation, Hair Growth, and Hair Quality by Dermal Cells," J. Investig. Dermatology, 100, pp. 229–236 (1993).

P.A. Brigham, et al., "The Stumptailed Macaque as a Model for Androgenetic Alopecia: Effects of Topical Minoxidil Analyzed by Use of the Folliculogram," Clinics in Dermatol., 6, pp. 163–168 (1988).

L.H. Kligman, "The Hairless Mouse as a Model for Evaluating Promoters of Hair Growth," Clinics in Dermatol., 6, pp. 163–168 (1988).

J.R. Matias, et al., "Animal Models of Androgen–Dependent Disorders of the Pilosebaceous Apparatus," ARch. Dermatol. Res., 281, pp. 247–253 (1989).

A.M. Hussein, et al., "Protection from Chemotheraphy–Induced Alopecia in a Rat Model," Science, 249, pp. 1564–1566 (1990).

U. Lichti, et al., "In Vivo Regulation of Murine Hair Growth: Insights from Grafting Defined Cell Populations onto Nude Mice," J. Investig. Dermatol, 101, pp. 124S–129S (1993).

S.H. Yuspa, et al., "Regulation of Hair Follicle Development: An in vitro Model for Hair Follicle Invasion of Dermis and Associated Connective Tissue Remodeling," J. Investig. Dermatol., 101, pp. 27S–32S (1993).

M.H. Philpott, et al., "An in vitro Model for the Study of Human Hair Growth," Annals of the New York Academy of Sciences, 642, pp. 148–164 (1991).

M.H. Philpott, et al., "Human Hair Growth in vitro," J. of Cell Science, 97, pp. 463–471 (1990).

A.B. Jahoda, "Dermal–Epidermal Interactions," Clinics in Dermatology, 6, pp. 74–82 (1988).

Hideo Uno and Sotaro Kurata, "Chemical Agents and Peptides Affect Hair Growth", The Society for Investigative Dermatology pp. 143S–147S (1993).

Hideo Uno "The stumptailed macaque as a model for baldness: effects of minoxidil" International Jour of Cosmetic Science 8, pp. 63–71 (1985).

P.L. Williams, et al., "Hairs" in Gray's Anatomy, pp. 90–94, edited by P.L. Williams, et al., Churchill Livingston (1989).

A. Tosti, et al., "Drug–Induced Hair Loss and Hair Growth," Drug Saf., 10, pp. 310–317 (1994).

F.J. Ebling, "Hair," J. Investig. Dermatol., 67, pp. 98–105 (1976).

F.J. Ebling, The Biology of Hair, Dermatological Clinics, 5, pp. 467–481 (1987).

R.L. Reid & D.A. Van Gugt, "Hair Loss in the Female," Obstetrical and Gynecological Survey, 43, pp. 135–141 (1988).

D.G. Brodland & S.A. Muller, "Androgenetic Alopecia (Common Baldness)," Cutis, 47, pp. 173–176 (1991).

K.E. Burke, "Hair Loss," Postgraduate Medicine, 85, pp. 52–77 (1989).

R.A. Ignotz, "TGF–B and Extracellular Matrix Related Influences on Gene Expression and Phenotype," Critical Reviews in Eukaryotic Gene Expression, 1, pp. 75–84 (1991).

M. Nilsen–Hamilton, "Transforming Growth Factor–B and Its Actions on Cellular Growth and Differentiation," Current Topics in Developmental Biology, 24, pp. 95–136 (1990).

M.B. Sporn & A.B. Roberts, "TGF–B: Problems and Prospects," Cell Regulation, 1, pp. 875–882 (1990).

Kohei Miyazono et al. "Latent forms of TGF–B: molecular structure and mechanisms of activation", Clinical Applications of TGF–B, Wiley, Chichester (Ciba Foundation Symposium 157 pp. 81–87 (1991).

R.J. Akhurst et al. "The Role of TGF–Bs in Mammalian Development and Neoplasia", Molecular Reproduction and Development 32:127–135 (1992).

A.B. Leahey, et al., "Clinical Experience with n–butyl cyanoacrylate (Nexacryl) Tissue Adhesive," Ophthalmology, 100, pp. 173–180 (1993).

Meses, H TGF–B Regulation of Epithelial Cell Proliferation, Molecular Reproduction and Development 32:179–184 (1992).

Ralf Paus, et al. "The Induction of Anagen Hair Growth in Telogen Mouse Skin by Cyclosporine A Administration" Laboratory Investigation, vol. 60, No. 3, pp. 365–369 (1989).

Anita B. Roberts et al. "Multiple forms of TGF–B: distinct promoters and differential expression", 1991 Clinical applications of TGF–B, Wiley, Chichester (Ciba Foundation Symposium 157) pp. 7–28 (1991).

Michael Taylor et al. "Cyclosporin A Prolongs Human Hair Growth In Vitro", The Society for Investigative Dermatology, Inc. pp. 237239 (1993).

Andrezej Slominski et al. "Differential Expression and Activity of Melanogenesis–Related Proteins During Induced Hair Growth in Mice", The Society for Investigative Dermatology, Inc. pp. 172–179 (1991).

J Massague, et al. "Transforming Growth Factor–B", Cancer Surveys Bolume 12: Tumour Suppressor Genes, the Cell Cycle and Cancer, pp. 81–103 (1992).

R. Imai, et al. "Organ culture of human hair follicles in serum–free medium", vol Dermatology Research, Springer Verlag pp. 469–474 (1992).

Anita B. Roberts, et al. "Multiple forms of TGF–B: distinct promoters and differential expression", Clinical applications of TGF–B, Wiley, Chinchester (Ciba Foundation Symposium 157) pp. 7–28 (1991).

"Material Safety Data Sheet" by Tri–Point Medical (1993).

"Material Safety Data Sheet" by Sigma Chemical Company (1994).

John H. Exton "Messenger molecules derived from membrane lipids", Current Opinion in Cell Biology 6:226–229 (1994).

Rogaine® Patient Information Booklet, The Upjohn Co., Kalamazoo, MI, revised Jun., 1992.

The Nexaband Family of Adhesives, Tri–Point Medical L.P. Raleigh NC 27604 (1991).

FIGURE IA
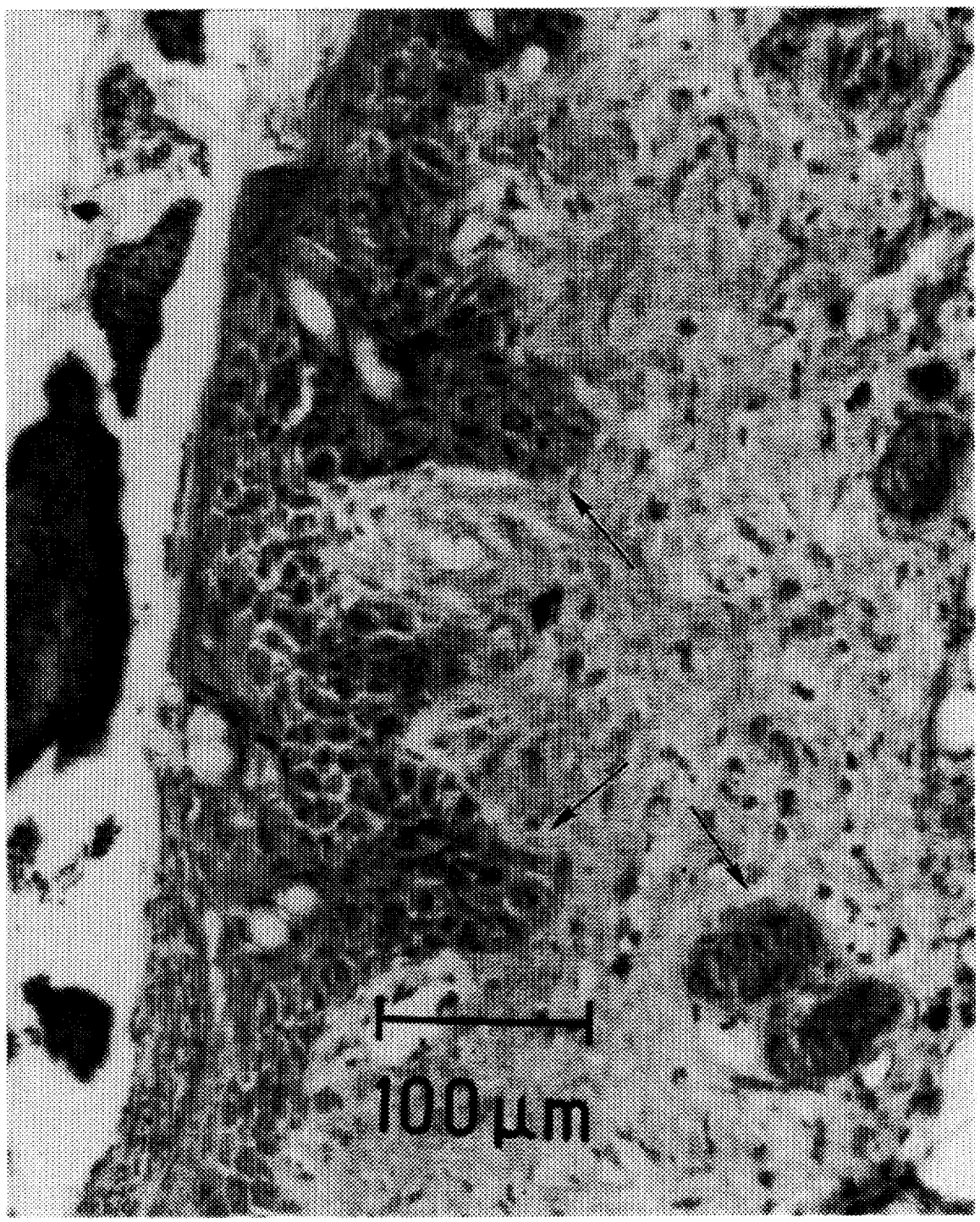

Fig. 3B. Thickness of Dermis Layer

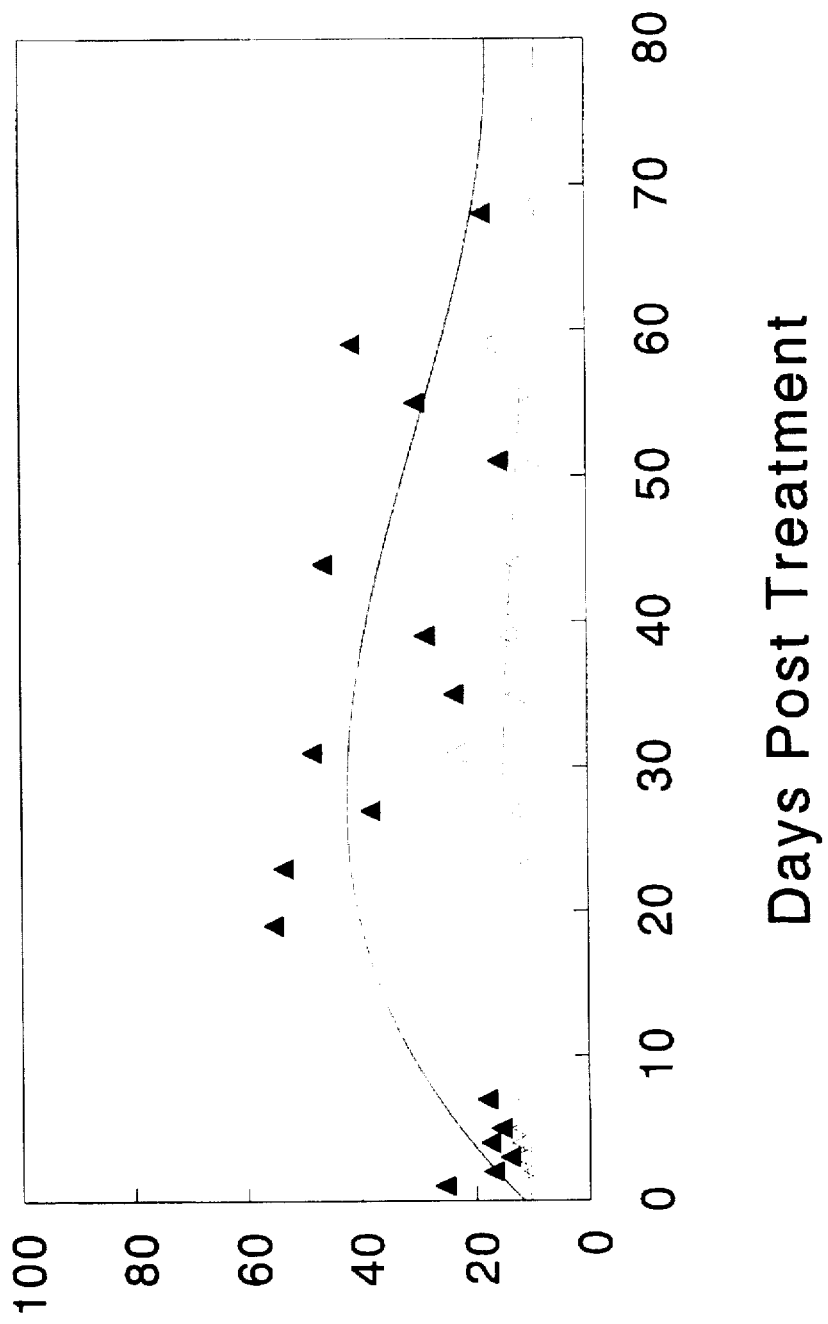
FIGURE 6 I3
Fig. 6B. Hair follicle number in the treated and untreated skin

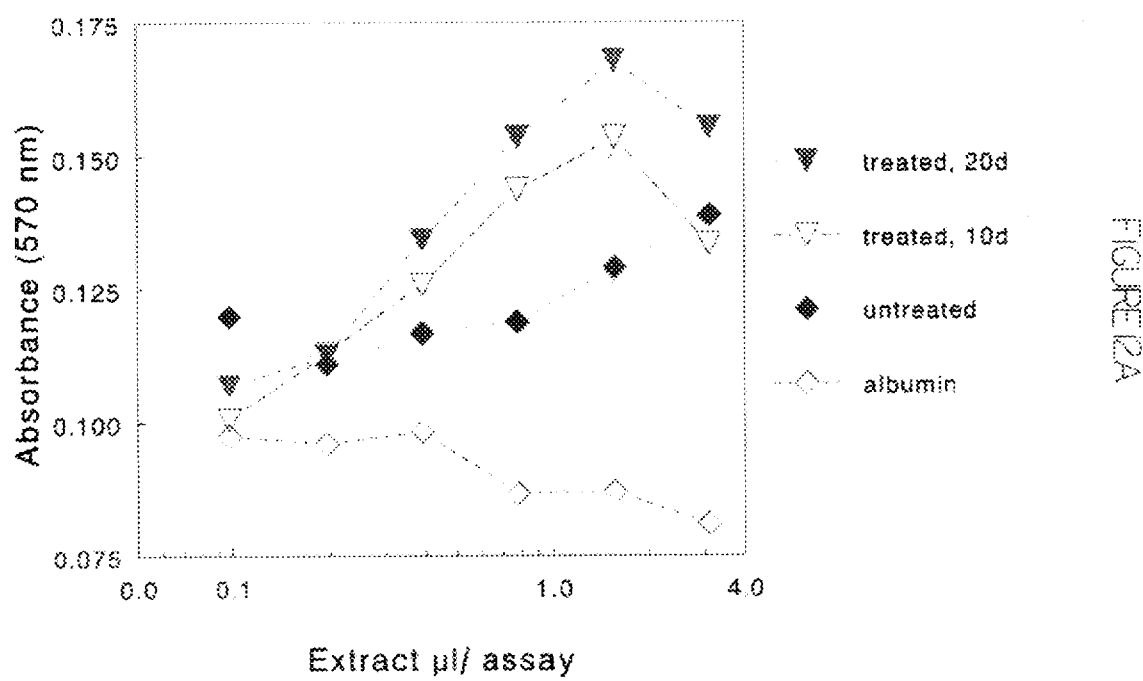
Fig. 12A. Effect of the extract of the treated skin on cell proliferation

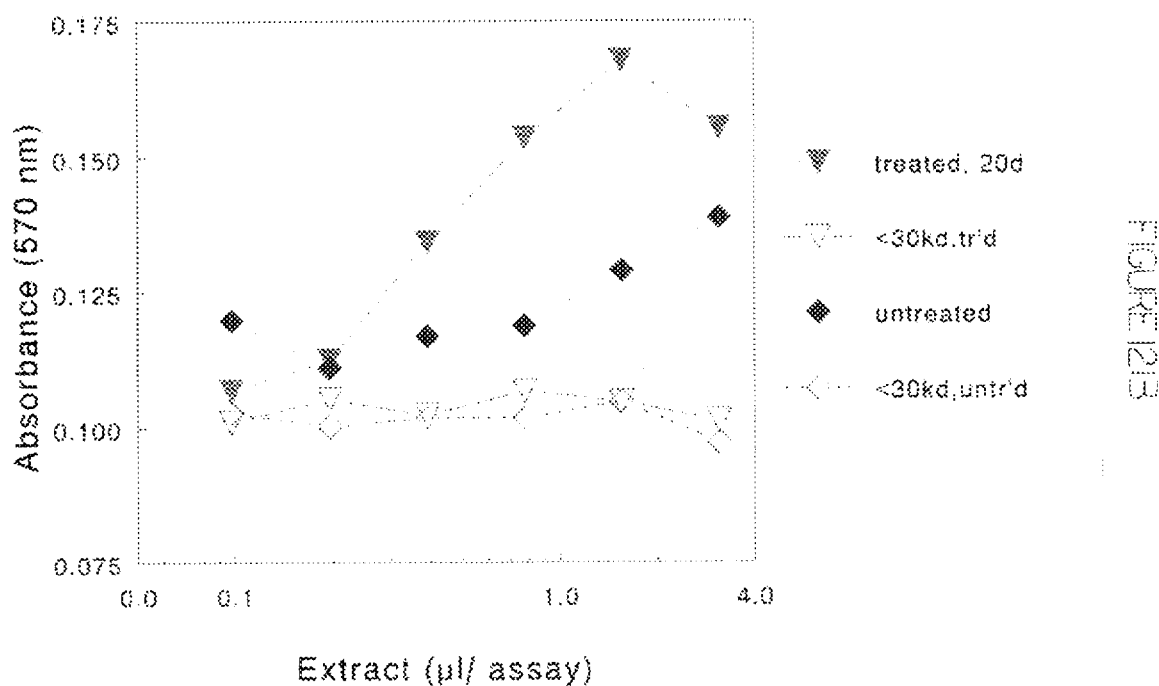
Fig. 12B. Effect of the extract without molecules larger than 30 kD

COMPOSITION AND METHODS FOR STIMULATING HAIR GROWTH

BACKGROUND OF THE INVENTION

1. Field of the Invention

This invention relates generally to the stimulation of hair growth in animals. In particular, this invention relates to the stimulation of hair growth in mammals by the application of a trichogenic formulation.

This invention also relates to a method for stimulating hair growth in mammals, involving the application of a trichogenic formulation to the skin, a method for increasing the rate of hair shaft elongation, a method for inducing the de novo development of hair follicles, a method for increasing the number of hair follicles present in the treated skin, a method to induce hair growth along a surgical incision, a method to improve hair regrowth in a healed wound site, a method to keep hair in subjects who receive chemotherapy or radiotherapy, a method for establishing animal models for research on hair follicle development and formation, a method for establishing animal model for research on melanogenesis metabolism, and a method for establishing experimental models to study cytokine production and cell proliferation.

2. Background of the Related Art

Hair loss and baldness (alopecia) are common phenomena in mammals, including humans. (see, for example, A. G. Messenger (1993) *J. Investig. Dermatol.* 101:4S-9S; R. P. R. Dawber (1987) *Dermatologica* 175:23-28; D. G. Brodland, S. A. Muller (1991) *Cutis* 47:173-176; J. R. Spindler, J. L. Data (1992) *Dermatol. Nurs.* 4:93-99; A. K. C. Leung, W. L. M. Robson (1993) *J. Roy. Soc. Health* 113:252-256). Hair loss may be naturally occurring (primary alopecia) or it may be induced by chemical or physical agents (secondary alopecia). See, for example, M. B. Brodin (1987) *Dermatol. Clin.* 5:571-579; A Tosti, et al. (1994) *Drug Saf.* 10:310-317; H. J. Carson, et al. (1994) *J. Cutan. Pathol.* 21:67-70. Hair loss may also result from specific disease states, such as mange, or formation of scar tissue from bites, and with increasing age (D.A. Mehregan, et al. (1992) *J. Am. Acad. Dermatol.* 27:935-942; D. A. Slagle, T. A. Martin (1991) *Am. Fam. Physician* 43:2019-2024; L. V. Spencer, J. P. Callen (1987) *Dermatol. Clin.* 5:565-570. Hair loss is an extremely common condition in healthy adult male humans, and occurs frequently in adult female humans. In fact, some degree of alopecia on the vertex from puberty onwards is thought to be a universal phenomenon in both men and women (R. P. R. Dawber (1987) *Dermatologica* 175:23-28). Alopecia is also frequently observed in both pre- and post-pubertal patients as a side effect of anti-cancer chemotherapy (A. M. Hussein, et al. (1990) *Science* 249:1564-1566; B. W. Cline, (1984) *Cancer Nursing* 7:221-228; A. F. Hood (1986) *Med. Clin. North Am.* 70:187-209).

The physical phenomenon of hair loss may lead to psychological problems in the patient, decreased social activity, and the development of psychological diseases. In the case of cancer patients, the likelihood of chemotherapy-induced alopecia may lead to a refusal to accept treatment. As a result of the prevalence of alopecia, and its potentially devastating impact, there is immense interest in the development of effective clinical treatments, both to prevent hair loss and to stimulate regrowth of lost hair.

Abnormal hair loss in animals is also commonly observed, and is associated with certain disease conditions, including skin wounds and mange. Hair growth in domestic animals is of economic concern, both from a cosmetic standpoint in pets and show animals, and in the production of fiber and pelts used in the textiles and garment industries. Many domesticated animals (e.g. sheep) are used as a source of fiber, including wool and fur. The coat is either harvested (clipped) on a periodic basis throughout the life of the animal, such as in the case of sheep; or the pelage together with the skin is removed following sacrifice, e.g. mink. The skin of many domesticated animals is used as a commercial source of leather and suede. These materials are manufactured directly from the skin of an animal by the process of tanning. Therefore, improvements in the quality and thickness of skin prior to sacrifice can benefit the commercial production of skin-derived products. Furthermore, many animals, especially those with pedigrees, are shown publicly in competitions for judgement of the best specimen in their class. Such animals include, but are not limited to, the following categories: horses, cattle, sheep, dogs, cats, and rabbits. In many instances, an important criterion on which judgement is based is the appearance of the coat or pelage. Thus there is a need for physiologically effective treatment to improve the nature and appearance of animal coats during the life of the animal.

Despite the widespread occurrence of alopecia, the need for prevention and therapy, and extensive research efforts to find suitable remedies, there remains an urgent need for effective treatment. For example, lack of a proven and effective treatment for alopecia has caused many afflicted individuals to adopt the practice of wearing a wig or toupee. Another extreme measure used to combat alopecia, hair transplant surgery, is not available as an option in many cases, e.g. following chemotherapy, and offers, at best, only a partial remedy. At the same, the latter treatment suffers from a number of disadvantages, including the need for surgery.

A common non-surgical treatment for stimulating hair growth which is currently used clinically is minoxidil (The Upjohn Company, Kalamazoo, Mich.). A solution of minoxidil as active ingredient is known as Rogaine®. As stated in the Rogaine® Patient Information Booklet (The Upjohn Company, Kalamazoo, Mich., revised June, 1992) minoxidil is a vasodilatory drug which has serious side effects when administered orally for the treatment of hypertension. At the same time, topical application of minoxidil for the treatment of alopecia is only partially effective and suffers from a number of disadvantages. For example, it is only recommended for treatment of male pattern alopecia of the vertex (cf. frontal recession), has to be applied twice daily for at least four months, and requires a normal scalp with no local abrasions, dermatitis or sunburn—conditions that can increase absorption into the blood stream and the concomitant risk of side effects. Further, minoxidil is of limited effectiveness: based on the investigator's evaluation, there is no significant increase in terminal hair regrowth between minoxidil and placebo treatment groups after four months of treatment (refer to the Rogaine® Patient Information Booklet, The Upjohn Company, Kalamazoo, Mich., revised June, 1992). In patients who do respond to minoxidil treatment, the new hair is likely to be shed within a few months after stopping treatment. Likewise, the effect of minoxidil in stimulating hair growth in a macaque monkey model was found to be transient: substantially all hair grown during minoxidil treatment was lost within six months of treatment being discontinued (P. A. Brigham, et al. (1988) *Clinics in Dermatol.* 6:177-187).

SUMMARY OF THE INVENTION

The methods and compositions of the present invention may be used to promote hair growth/regrowth in adult mammals. The instant methods, and compositions used therein, also induce major physiological, developmental, and structural changes in the skin of adult mammals including: skin differentiation, wound tissue remodelling in healed incision/excision wound sites, follicle development and regeneration, an increase in the number of hair follicles, morphological and functional change of hair follicles in different stages of the hair cycle, melanogenesis, hair shaft elongation, and accelerated hair growth rate. The methods and compositions of the present invention demonstrate the involvement of various growth factors in follicular development and regulation of the hair growth cycle. The methods and compositions of this invention also demonstrate hair follicle differentiation and the hair growth process in adult mammals in response to a single application of an extraneous composition.

In accordance with one embodiment of the invention, the hair growth stimulating method comprises topically treating the area of skin affected by hair loss. The method may comprise topical treatment as a single application, or it may comprise periodic treatment over an extended treatment time period as needed. Alternatively, the method may include a slow-release mechanism from a suitable carrier, or via any of several drug delivery mechanisms known in the art.

In accordance with a method of the invention, a trichogenic composition may be applied at the point of an incision in the skin. Such an incision may be made by a scalpel as a part of the treatment protocol, in order to induce regeneration or the de novo development of hair follicles within the dermis and subcutaneous layer. Alternatively, an incision may pre-exist, for example, due to cranial or facial injury, prior to treatment with the hair growth stimulator.

In accordance with an embodiment of the invention, a trichogenic composition may be applied at the site of an excision in the skin. Such an excision may be due to various accidental injuries to the cranium, face, arm, leg, etc., in order to induce new hair follicle formation and to promote tissue remodeling to normal in the wounded site.

In accordance with a method of the invention, a trichogenic composition may be applied during or after plastic surgery at the sites of eyebrow, mustache, or beard to improve cosmetics.

In accordance with an embodiment of the invention, the method may be applied to a subject who is receiving chemotherapy or radiotherapy and suffering hair loss. Such a situation may occur as a part of cancer treatment protocol, in order to induce hair follicle formation. The embodiment of the invention also includes the situation that the hair growth stimulator can be used for the subject who is going to receive chemotherapy or radiotherapy, to avoid hair loss, or who received chemotherapy or radiotherapy before and is suffering a permanent hair loss. Alternatively, the hair growth stimulator may be used on a subject who suffers hair loss from exposure to a toxic chemical or radioactive source. Such a situation may result from an industrial toxic chemical accident, explosion of chemical or nuclear plant, or accidental administration of toxic chemicals or toxic drugs.

In accordance with still another embodiment of the invention, the method may include administration by subcutaneous injection to the treatment area.

Those skilled in the art of drug application know how to determine the manner and frequency of application, the formulation of the active ingredient, and the dose will be varied according to the nature and severity of the condition being treated, the area of skin affected, and the like.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1A is a photomicrograph of epidermis and dermis of a C57BL/KsJ db/+ mouse 3 days after n-butyl cyanoacrylate application, with the surface of the skin at the top. Epithelial pegs project into the dermal layer, and antibody to TGF-$\beta$1 is localized in the epidermis and hair follicles in the dermis (see brown stain). The arrows indicate examples of the stain in epithelial pegs and hair follicles. The bar represents 100 $\mu$m.

FIG. 1B is a photomicrograph of a skin section of a C57BL/KsJ db/+ mouse 3 days after n-butyl cyanoacrylate application, showing the demarcation between the treated area (left side) and the untreated area (right side). The treated area (big arrows) has a multilayered epidermis, thickened dermis, and epidermal peg elongation. The small arrows indicate examples of epidermal peg elongation. The bar represents 100 $\mu$m.

FIG. 6B is a graph comparing the hair follicle number between the n-butyl cyanoacrylate-treated and adjacent untreated skin. In the diabetic strain C57BL/KsJ db/db, the maximum number of hair follicles in treated areas (filled triangles) is about 4 fold that of untreated areas (open triangles). Each time point represents 2–6 mice.

FIG. 12A is a graph comparing the effect of extracts of skin treated with n-butyl cyanoacrylate and of untreated skin in a cell proliferation assay. The filled triangles indicate extracts of treated tissue harvested at day 20 post-treatment. open triangles denote treated tissue harvested at day 10. Filled lozenges denote untreated tissue harvested at day 20, and open lozenges are the mouse albumin control.

FIG. 12B is a graph comparing the effect of extracts of skin treated with n-butyl cyanoacrylate and of untreated skin, with and without fractionation to exclude molecules larger than about 30 kDa, in a cell proliferation assay. The filled triangles indicate extracts of treated tissue harvested at day 20 post-treatment. Open triangles are the filtrate of the treated tissue harvested at day 20. Filled lozenges are the untreated tissue harvested at day 20. open lozenges denote the filtrate of the untreated tissue extract. The filtration step removes stimulation, indicating that the proliferative agent or agents are larger than 30 kDa in mass.

DETAILED DESCRIPTION OF THE INVENTION

A. Terminology

Figure 11B:
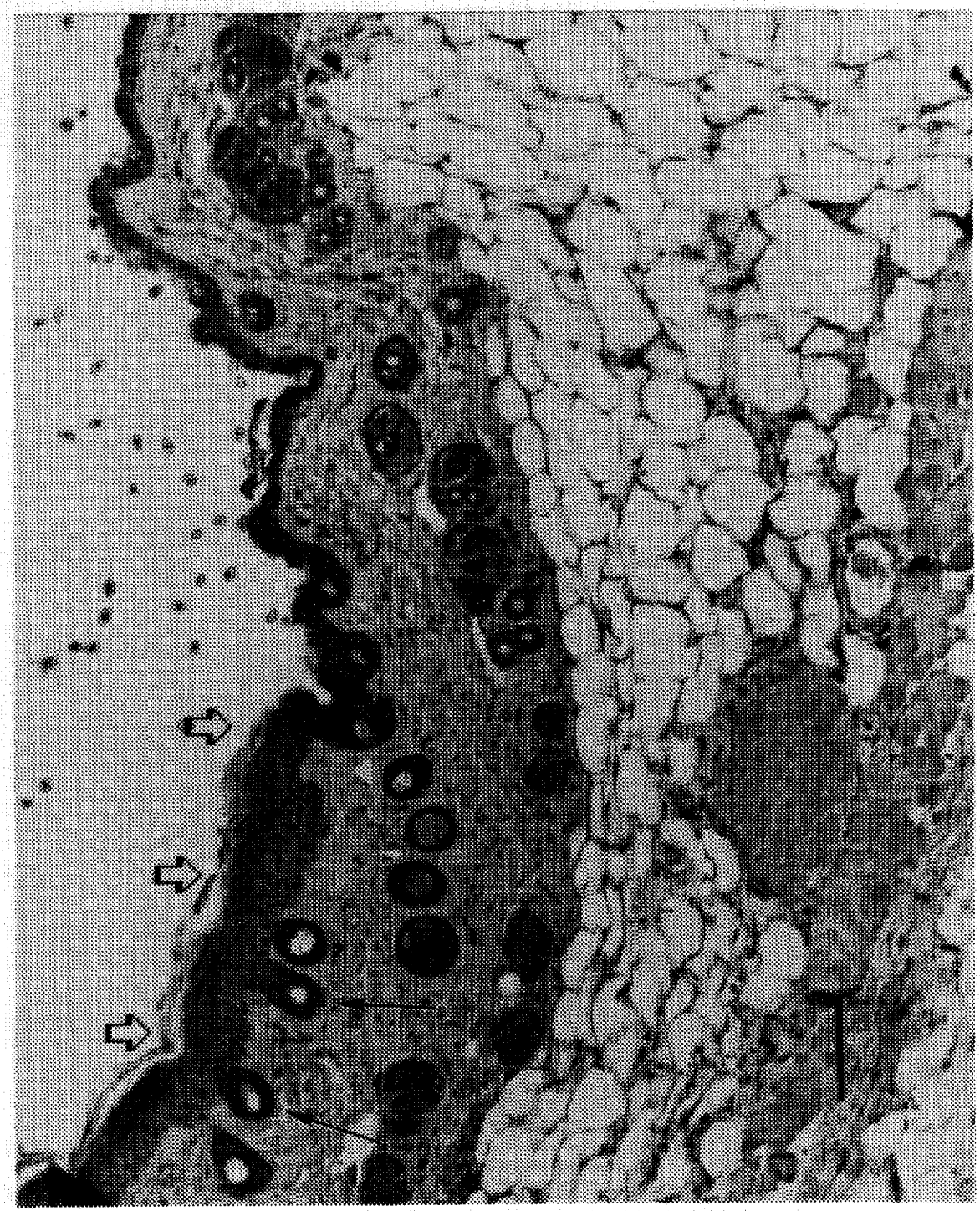
FIG. 11 is a photograph of the organ culture of skin not treated, and adjacent skin treated with n-butyl cyanoacrylate then cultured in Dulbecco's Modified Eagle Medium supplemented with 10% fetal bovine serum. At 14 days in organ culture after treatment hair growth is apparent in the treated area (arrow), but the adjacent untreated part of the skin is hairless.

The term "hair" as used herein shall mean filamentous appendages from the skin of vertebrates, including the pelage, coat, fur or wool of mammals, and the feathers of birds.

The term "hair growth" as used herein shall mean any increase in the total quantity of hair, an increase in the number of active hair follicles, an increase in the number of terminal hairs, an increase in the length of one or more hair shafts, an increase in the rate of hair shaft elongation, or an increase in the diameter of one or more hair shafts, on a given area of skin.

The term "hair growth cycle" as used herein shall mean progression through the phases known as anagen, the growth phase; catagen, the regressing phase; and telogen, the resting phase. The length of each phase varies with species, strains, individuals, and body site; as well as environmental factors, intrinsic hormone levels, and other factors.

The expression "terminal hair" as used herein shall mean readily visible, relatively coarse hair that is typically pigmented; such as that normally found on the scalp of young adult humans. In animals, terminal hairs comprise the pelage and whiskers. Terminal hair is contrasted with "vellus hair" which is extremely fine, short, unpigmented and almost invisible.

The term "hair loss" as used herein shall mean a net decrease in the amount of hair, in the number of terminal hairs, or in the number of hair follicles, on a given area of skin.

The term "alopecia" as used herein means a condition in which hair is being lost or has been lost, or a pre-existing condition of congenital baldness.

The term "growth factor" as used herein means a biologically active substance which influences proliferation and/or differentiation of various cell types, and may effect developmental, morphological and functional changes, either alone or when modulated by other substances. A growth factor herein may be a proteinaceous entity comprising one or more polypeptide chains.

The term "TGF" as used herein means generally transforming growth factor, and may refer to one or more members of the class of transforming growth factors, or collectively to the entire class of transforming growth factors.

The expression "de novo hair follicle differentiation" as used herein means the formation of new hair follicles, as a result of the proliferation of germinative cells and the further differentiation of mesenchymal cells in the proximity of the germinative cells.

The term "trichogenically effective amount" means that amount which is effective in increasing: the total amount of hair, the overall length or diameter of one or more hairs, the total number of terminal hairs, the total number of hair follicles, or the ratio of hair follicles in anagen:telogen. Such effects may be due to prolongation of the anagen phase, delay in the transition from anagen to telogen, or de novo hair follicle development.

As used herein, a "physiologically effective formulation" is a composition that stimulates an increase in hair growth of an animal, or improves the overall appearance of the pelage of an animal, or hair of a human.

B. General Methods

The skin or integumentary system is the largest organ of the human body. It acts as an interface between the internal and external environment, and fulfills thermoregulatory, barrier, and sensory functions, among others. Histologically, three major tissue layers are identified. The uppermost layer, the epidermis, is a relatively thin stratified squamous epithelium which is itself composed of five strata. Subjacent to the epidermis is the dermis, a dense fibroelastic connective tissue stroma. The third layer, lying beneath the dermis is the subcutaneous layer composed of fatty connective tissue.

There are two types of skin: hair-bearing skin, which covers the vast majority of the body surface; and hairless skin confined to areas such as the palms of the hands, soles of the feet, and mucous membranes. The two skin types are differentiated on the basis of the presence or absence of the pilosebaceous apparatus: the hair follicle and the accompanying sebaceous gland.

Hairs (or pili) are filamentous, keratinized structures derived from the epidermis. Hairs have a number of roles, including thermoregulation, sensory perception, and social communication. The density of hairs per unit area of skin varies with species, strain, and skin site. For example in humans, it ranges from about 600 $cm^{-2}$ to about 60 $cm^{-2}$, with the highest density being on the face.

Hairs show enormous variation in the length and diameter of the hair shaft: from <1 mm to >1,000 mm in length, and from 0.005 mm to 0.5 mm in diameter. There are also major differences, within a given individual, in the degree of pigmentation. Two broad categories of hairs are recognized: vellus hairs are short and narrow, and are present over most of the body surface; while terminal hairs are longer, thicker, and often heavily pigmented. Terminal hairs include those of the scalp, eyebrows and eyelashes, as well as the post-pubertal hair of the axillae and pubis, and the facial and body hair in many males.

Each hair consists of a shaft and a root. The hair shaft is composed of specialized cells (keratinocytes) containing a particularly strong form of keratin, providing a filament of material with high tensile strength. The root lies within the hair follicle, which is an invagination of the epidermis. The hair follicle may extend deeply into the hypodermis or may be more superficial in the dermis. The proximal end of the root is expanded to form the hair bulb. The bulb is deeply indented on its deep surface by a conical vascular dermal papilla. (For a general description of the components of the skin, its appendages, and the pilosebaceous apparatus see, for example, R. F. Oliver (1980) in The *Skin of Vertebrates* pp. 199–213, edited by R. I. C. Spearmen & P. A. Riley, Academic Press; and P. L. Williams, et al. (1989) *Hairs in Gray's Anatomy*, pp. 90–94, edited by P. L. Williams, et al., Churchill Livingston).

The hair bulb comprises the germinative matrix, a zone of great mitotic activity which generates the hair and its surrounding inner root sheath, and the keratogenous zone, in which cells are keratinized. The germinative matrix consists of a mass of pluripotent cells capping the dermal papilla. Cells arising mitotically from this group move apically, and may differentiate along several different routes. The activity of the hair bulb, and of the whole root complex involves various morphogenetic processes in which different cell shapes, chemical forms of keratin, and cellular migration patterns are produced.

The formation of hair follicles results from interactions between the epidermis and mesenchyme during fetal development (R. F. Oliver & C. A. B. Jahoda (1988) *Clinics in*

*Dermatology* 6:74–82). The dermal components of the hair follicle, namely the dermal papilla and dermal sheath, are derived from an aggregate of mesenchymal cells. Follicle initiation and development begin with the aggregation of dermal fibroblasts and epidermal keratinocytes. The epidermal cells proliferate and penetrate the dermis as plugs. Subsequently, the epidermally derived cells encircle a dermal aggregation and incorporate it into a pocket of tissue, the dermal papilla.

It is known that follicular development relies on a series of messages between dermis and epidermis. The initial, dermis-derived message is common, not only within mammalian species, but to all classes of vertebrate. The next signal, from the epidermis is class-specific, and instructs the dermis to form a dermal papilla. Thereafter, a second dermal message instructs the epidermal placode to form the class-specific appendage (e.g. hair in mammals) (see, for example, A. G. Messenger (1993) *J. Investig. Dermatol.* 101:4S-9S; D. L. du Cros (1993) *J. Investig. Dermatol.* 101:106S-113S).

Grafting studies have shown that the dermal papilla is necessary for normal hair follicle function and production of the shaft. The dogma regarding hair follicle development in an individual is that the population of hair follicles and dermal papillae is established during embryogenesis with no further development subsequent to the first few days after birth (P. L. Williams, et al. (1989) Hairs in *Gray's Anatomy*, pp. 90–94, edited by P. L. Williams, et al., Churchill Livingston; D. H. Cormack (1987) Hairs in *Ham's Histology* 9th Ed., ed. by D. H. Cormack, pub. J. B. Lippincott Co.).

Hair growth is effected by proliferation of the hair follicle matrix cells under control of the dermal papilla, and is cyclical. Three distinct stages in the hair growth cycle are recognized: anagen, an active phase when hair growth occurs; catagen, the transition stage during which follicle activity declines; and telogen, the resting phase when no cell proliferation occurs. In simple terms, alopecia can be explained as degeneration of the hair follicles and a shift in the population of follicles from the anagen phase to the telogen phase.

The dynamics of the hair growth cycle vary from species to species, between different body sites of the same species, and between different follicle types in the same body site. Synchrony of the hair growth cycle during the neonatal period occurs in many animals, including humans. In many mammals, characteristic molt waves continue into adult life. In many wild species, the molt is regulated by environmental stimuli, particularly the photoperiod, resulting in seasonal changes in the quality and quantity of the pelage. In humans, follicular activity rapidly becomes asynchronous, and local mechanisms of control of the hair cycle predominate. However, systemic modulation of the human hair growth cycle does occur during pregnancy and postpartum. It is also reported that human hair growth does show vestiges of seasonal variation (A. G. Messenger (1993) *J. Investig. Dermatol.* 101:4S-9S). In the mouse, the first follicles to appear during embryogenic development are those of the vibrissa on the snout. Of the pelage follicles, up to 30% are initiated prenatally, and the remainder develop within the first few days following birth. Mature murine pelage follicles undergo a hair growth cycle of approximately four weeks duration. The various phases of the hair growth cycle are accompanied by characteristic changes in the thickness of the epidermis, dermis, and adipose layer (D. L. du Cros (1993) *J. Investig. Dermatol.* 101:106S-113S).

Numerous factors may be involved in regulating the proliferation of hair follicle matrix cells, and controlling the hair growth cycle. For example, various growth factors, steroid hormones, dermo-epithelial interaction, and the immune system have been implicated. An increased vascularity in the dermis is known to stimulate hair growth (J. R. Matias, et al. (1989) *Arch. Dermatol. Res.* 281:247–253).

Growth factors are secretory molecules, generally polypeptides, which mediate intercellular communication in metazoans. Thus, various growth factors have been implicated in the control of complex processes occurring during embryogenic development and in tissue repair and regeneration (J. Massague (1990) *Annu. Rev. Cell Biol.* 6:597–641). In addition, most of the major growth factor families and their receptors have been implicated in regulating skin cell function, including for example: epidermal growth factor (EGF), keratinocyte growth factor (KGF), transforming growth factor-$\alpha$ (TGF-$\alpha$), transforming growth factor-$\beta$ (TGF-$\beta$), fibroblast growth factor (FGF), bone morphogenetic protein-4 (BMP-4), and insulin-like growth-1 (IGF-1) (see A. G. Messenger (1993) *J. Investig. Dermatol.* 101:4S-9S; D. L. du Cros (1993) *J. Investig. Dermatol.* 101:106S-113S and references cited therein). Furthermore, several growth factors have been implicated in hair follicle morphogenesis and/or control of hair growth, including EGF (D. L. du Cros (1993) *J. Investig. Dermatol.* 101:106S-113S; A. G. Messenger, *J. Investig. Dermatol.* 101:4S-9S; M. P. Philpott, et al. (1990) *J. Cell Science* 97:463–471), FGF (D. L. du Cros (1993) ibid.), and KGF (G. F. Pierce, et al. (1994) *J. Exp. Med.* 179:831–840), and TGF-$\beta$ (A. G. Messenger (1993) ibid.; M. P. Philpott, et al. (1990) ibid.).

Studies of the induction of hair follicle development and of the hair growth cycle have been hampered, in part, by the lack of suitable in vivo animal models, and by the paucity of appropriate in vitro experimental systems. Numerous species and strains of animals have been used to investigate the hair growth process in vivo and/or to simulate human alopecia. Most studies have focused on either new-born or weanling rats and mice, genetically impaired or mutated mice, or stump-tailed macaque monkeys.

Members of a macaque species native to S.E. Asia, which show a balding pattern similar to that associated with human androgenetic alopecia, were used by Brigham et al. to study the effect of topical minoxidil on the balding process analyzed by folliculogram (P. A. Brigham, et al. (1988) *Clinics in Dermatology* 6:177–187). A. M. Hussein et al. (A. M. Hussein, et al. (1990) *Science* 24:1564–1566) used young (6–8 day old) rats, treated with cytosine arabinoside, doxorubicin or cyclophosphamide, as a model for chemotherapy induced alopecia (A. M. Hussein, et al. (1990) *Science* 24:1564–1566). A mutant strain of the mouse which expressed androgen-dependent baldness was developed by Matias et al. as a model of androgenetic alopecia (J. R. Matias, et al. (1989) *Arch. Dermatol. Res.* 281:247–253). Kligman used a hairless mouse strain as a model for evaluating hair growth promoters (L. H. Kligman (1988) *Clinics in Dermatology* 6:163–168). Neonatal mouse skin was used by du Cros (D. L. du Cros (1993) *Developmental Biology* 156:444–453) to investigate the influence of FGF in the development and cycling of murine hair follicles (D. L. du Cros (1993) *Developmental Biology* 156:444–453). The role of cyclosporin in hair growth was investigated by A. Gilhar et al. using human split-thickness skin grafts which were transplanted to nude rats (A. Gilhar, et al. (1990) *Dermatologica* 181:117–121), or to nude mice (A. Gilhar, et al. (1991) *Acta Derm. Venereol.* (Stockh) 71:327–330).

In vitro models include culture of excised, intact, human anagen hair follicles (M. P. Philpott, et al. (1990) *J. Cell*

Science 97:463–471); organ culture of human hair follicles in serum-free medium (R. Imai, et al. (1993) Arch. Dermatol. Res. 284:466–471); and the use of a collagen matrix system during culture of a heterogeneous preparation of murine hair follicles, or co-culture of murine hair follicle buds with immortalized rat vibrissa dermal papilla cells (S. H. Yuspa, et al. (1993) J. Investig. Dermatol. 101:27S-32S). All of the experimental models described above have one or more significant disadvantages and/or limitations to their use and effectiveness in studying mammalian skin differentiation and hair growth.

The present invention demonstrates cyanoacrylates as strong hair growth stimulators that can avoid the shortcomings of earlier procedures. The adhesive properties of certain cyanoacrylate esters was discovered by Coover in 1959 (H. W. Coover, et al. (1959) J. Soc. Plast. Eng. 15:5). Over the past two decades cyanoacrylates, in particular n-butyl cyanoacrylate and iso-butyl cyanoacrylate, have been widely used in surgery as tissue adhesives and as wound coverings (M. L. Ronis, et al. (1984) Laryngoscope 94:210–213; S. Sabanathan (1993) Eur. J Cardiothorac. Surg. 7:657–660; A. B. Leahey, et al. (1993) Ophthalmology 100:173–180). N-butyl cyanoacrylate has been used in more than one thousand eye surgeries and larynx repairs (see, for example, A. B. Leahey, et al. (1993) Ophthalmology 100:173–180, and references cited therein). Various formulations of cyanoacrylate (as the Nexaband® family of products, Tri-Point Medical, Raleigh, N.C.) are widely used in veterinary medicine as wound dressings.

The present invention provides for skin differentiation, hair follicle development, melanogenesis, and hair shaft elongation in adult mammals following treatment with a trichogenic composition. Several in vitro systems for investigating hair follicle growth exist, focusing on cell proliferation or hair shaft elongation, but not new follicle morphogenesis (S. Arase, et al. (1990) J. Dermatol. 17:667–676; R. Imai, et al. (1993) Arch. Dermatol. Res. 284:466–471; R. M. Philpott, et al. (1990) J. Cell Science 97:463–471). The invention is unique in providing the de novo differentiation and development of fully functional hair follicles in adult mammals.

Any of several laboratory animals may be used in conjunction with the present invention including, but not limited to, the Sprague-Dawley strain of rat, and the following strains of mice: C57BL/KsJ+/+, C57BL/KsJ db/+, C57BL/KsJ db/db, Balb/cBYj+/+, Balb/cBYj nu/+, HRS/J Hr/+, and RHJ LeJ hr$^{rh-j}$/+. Hair growth was profoundly stimulated locally in response to a single topical application of a formulation of a functional group derivative of a carboxylic acid. For example, a trichogenic formulation comprising an esterified derivative of acrylic acid may be used. In a preferred embodiment a formulation of butyl cyanoacrylate is found to be effective. Either a formulation of n-butyl cyanoacrylate or a formulation of iso-butyl cyanoacrylate may be used. In each case, the butyl cyanoacrylate is formulated with a suitable stabilizer to prevent spontaneous polymerization.

Preparations of a trichogenic composition comprising a functional group derivative of a carboxylic acid which is labile or tends to polymerize may be formulated with a suitable stabilizer to inhibit or delay chemical change to the active ingredient. In the case of n-butyl cyanoacrylate and iso-butyl cyanoacrylate, effective stabilizers are dibutyl sebacic acid and methyl hydroquinone, respectively.

Compositions comprising a functional group derivative of a carboxylic acid, with or without a suitable stabilizer, may be formulated with a suitable carrier material or diluent. Carriers may be used as an aid in application of the active ingredient to the treatment site or to dilute the active ingredient to provide an appropriate dose. Examples of suitable carriers include various oils, including various vegetable oils and mineral oils, waxes, and various organic solvents such as dimethyl sulfoxide and acetone. The list is not inclusive.

Suitable carriers may also comprise ingredients commonly used in the cosmetics industry. Thus physiologically acceptable carriers may be solids or liquids and may include solvents, diluents, humectants, and emollients. Such carriers may be used singly or in combination. Suitable carriers may include, but are not limited to, the following examples:

Solvents and diluents, for example,
castor oil,
ethylene glycol monobutyl ether,
diethylene glycol monoethyl ether,
dimethyl formamide,
corn oil,
dimethyl sulfoxide,
mineral oil,
soybean oil,
tetrahydrofuran, Emollients, for example,
cetyl palmitate,
dimethylpolysiloxane,
glyceryl monoricinoleate,
glyceryl monostearate,
isobutyl palmitate,
isocetyl stearate,
isopropyl palmitate,
isopropyl stearate,
butyl stearate,
isopropyl laurate,
hexyl laurate,
decyl oleate,
di-n-butyl sebacate,
isopropyl myristate,
lanolin,
lauryl lactate,
mink oil,
palmitic acid,
polyethylene glycol,
stearic acid,
sesame oil,
coconut oil,
arachis oil,
castor oil,
mineral oil,
isostearic acid,
palmitic acid,
isopropyl linoleate,
lauryl lactate,
myristyl lactate,
decyl oleate,
myristyl myristate, Formulation of the active ingredient for application to skin under the invention can also include ingredients to preserve the components of the formulation of the active ingredient and to prevent proliferation of microorganisms. Preservation by the inclusion of chemical preservatives and water activity depressants are well known in the cosmetic, food and pharmaceutical industries. Components of the formulation can be preserved by the inclusion of a suitable concentration of a chemical preservative, such as benzoic acid, sodium benzoate, potassium sorbate, propionic acid, and C1 to C4 esters of p-hydroxybenzoic acid. The composition can also be preserved by the inclusion of a water activity depressant in an amount sufficient to depress the water activity ($a_w$) value to <0.9, more preferably to <0.85. Examples of water activity depressants include sorbitol, propylene glycol, sugars, and alkali metal salts, including carboxylates, halides, and sulfates.

The active ingredient plus stabilizer may be soluble or insoluble in a liquid carrier. If the active ingredient and stabilizer compound are both soluble in the carrier, the carrier acts as solvent for the active ingredient. If the active ingredient and stabilizer are both insoluble in the carrier, they are dispersed in the carrier by means of, for example, a suspension, emulsion, gel, cream or paste, and the like. A preferred form of carrier, solvent or diluent for the active ingredient is in the form of an oil, including either light or heavy mineral oil. Vegetable oils, such as oils obtained from any of corn, sunflower, safflower, soybean, canola, and the like, may also be used.

Delivery of the formulation may also be via a slow-release mechanism, such as a dermal patch, or other mechanism well known in the art (see, for example, M. A. Longer & J. R. Robinson (1990) in *Remington's Pharmaceutical Sciences*, ed. by A. R. Gennaro, Mack Publishing Co.).

The trichogenic composition may also be formulated with an anti-inflammatory agent, for example an antihistamine. Alternatively, the subject may be treated with an anti-inflammatory material following treatment with the trichogenic agent.

The above list of carrier materials and methods for drug delivery is not meant to be exhaustive, but is presented merely for illustrative purposes and should not be construed as limiting the invention in any way. Those skilled in the art will realize that conventional carrier materials and drug delivery mechanisms may be used within the scope of the invention.

In the present invention, increased hair growth is readily observed in mammals following treatment with the formulation known as Nexaband® Liquid (Tri-Point Medical, Raleigh, N.C.). This composition is comprised of n-butyl cyanoacrylate (>85%), sebacic acid dibutyl ester (ca. 15%), as an inhibitor of spontaneous polymerization or stabilizer, and a small amount of a blue, FDA-approved dye. The mammals here are a rat and multiple strains of mice. In subsequent tests, the application of Nexaband® Liquid gave a universal, consistent and strong response: manifest as greatly increased hair growth at the site of application. The application here means, but is not limited to, the following situations: topical application on the intact surface of normal skin; topical application on the intact surface of the skin of mammals that are systemically pre-treated with anticancer drugs (and thereby hair regrowth and/or melanogenesis metabolism is inhibited); application to a full-thickness incisional or excisional wound; and application to the dermis layer by subcutaneous injection.

The trichogenic effect of n-butyl cyanoacrylate is at least twofold: 1) existing hair follicles are stimulated to grow hair at an accelerated rate, and 2) development of hair follicles is induced de novo. Induced hair follicles subsequently mature and produce terminal hairs. These findings are unexpected and surprising to us, because popular opinion dictates that hair follicle development only occurs during pre- and neo-natal periods and not in the adult. Nevertheless, all of the morphogenetic events related to pre-natal hair follicle development are accomplished by our invention.

Application of a formulation of iso-butyl cyanoacrylate, containing trace amounts (about 0.01%) of monomethyl hydroquinone as stabilizer, gave a positive response in the form of increased hair growth in, for example, several strains of mice. The response to iso-butyl cyanoacrylate in mice and rats was very similar to the response of hair growth induced by n-butyl cyanoacrylate.

In contrast, the stabilizer, sebacic acid dibutyl ester, the surgical adhesive Rezifilm® (which contains methyl acrylate), and the adhesive Weldwood® were not effective in stimulating hair growth. Similarly, 2% minoxidil (Rogaine®, The Upjohn Company, Kalamazoo, Mich.), applied topically once daily for 20 days in an amount of 20 $\mu l\ cm^{-2}$, was not effective in inducing hair growth.

These observations show that the chemical structure responsible for the observed effects is that of a functional group derivative of a cyanocarboxylic acid.

In a preferred embodiment, the active ingredient is a functional group derivative of an unsaturated cyanocarboxylic acid with the general formula, Formula I:

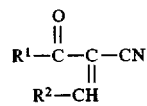

wherein $R^1$ is an ester of $C_1$–$C_{20}$ alkyl, cycloalkyl, alkenyl, alkynyl, aryl, alkaryl, aralkyl, hydroxyalkyl, or mono- or poly-alkoxyalkyl, or $R^1$ forms an alkyl amide of $C_1$–$C_{20}$, a dialkyl amide of $C_1$–$C_{20}$, an alkoxyalkylamide of $C_1$–$C_{20}$, an anhydride of $C_1$–$C_{20}$, an acyl halide, or $R^1$ is an amino group; and $R^2$ is $C_1$–$C_{10}$ alkyl, cycloalkyl, alkenyl, alkoxyalkenyl, alkynyl, aryl, alkaryl, aralkyl, or H.

More preferably, the functional group derivative of a cyano-carboxylic acid is an unsaturated cyanocarboxylic acid ester of the formula, Formula II:

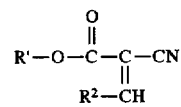

wherein $R^1$ is $C_1$–$C_{20}$ alkyl, cycloalkyl, alkenyl, alkynyl, aryl, alkaryl, aralkyl, or mono- or poly-alkoxyalkyl; and $R^2$ is $C_1$–$C_{10}$ alkyl, cycloalkyl, alkenyl, alkynyl, aryl, alkaryl, aralkyl, or H. Most preferably, $R^2$ is H, and $R^1$ is a C4 alkyl radical. Thus the most preferred cyanoacrylate ester is a butyl cyanoacrylate, either n-butyl cyanoacrylate:

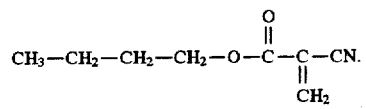

or isobutyl cyanoacrylate:

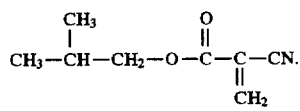

Thus $R^1$ groups in Formula II under the invention may include, but are not limited to, the following examples:

alkyl groups, for example, methyl, ethyl, propyl, butyl, pentyl; cycloalkyl groups such as cyclopropyl, cyclobutyl, cyclohexyl; alkenyl groups such as propenyl, butenyl, pentenyl; alkynyl groups such as propynyl, butynyl, pentynyl; aryl groups such as phenyl, biphenyl; monoalkoxyalkyl groups such as ethoxyethyl, methoxyethyl, ethoxymethyl;

polyalkoxyalkyl groups such as (ethoxyethyl)n; alkyl amide groups such as NH-propyl, NH-butyl; a dialkyl amide group such as N-dibutyl; and an alkoxyalkylamide group, such as N-ethoxyethyl.

According to one aspect of the invention, a trichogenic composition applied to skin under the invention may comprise mixtures of two or more cyanocarboxylic acid derivatives.

Compounds suitable for use in the present invention include:

ethoxyethyl 2-cyanoacrylate
butoxyethyl 2-cyanoacrylate
n-butyl 2-cyanoacrylate
isobutyl 2-cyanoacrylate
n-propyl 2-cyanoacrylate
isopropyl 2-cyanoacrylate
n-hexyl 2-cyanoacrylate
isohexyl 2-cyanoacrylate
cyclohexyl 2-cyanoacrylate
benzyl 2-cyanoacrylate
glycerol 2-cyanoacrylate
ethoxybutyl 2-cyanoacrylate
n-pentyl 2-cyanoacrylate
isopentyl 2-cyanoacrylate
n-heptyl 2-cyanoacrylate
isoheptyl 2-cyanoacrylate
n-octyl 2-cyanoacrylate
isooctyl 2-cyanoacrylate
n-nonyl 2-cyanoacrylate
isononyl 2-cyanoacrylate
n-decyl 2-cyanoacrylate
isodecyl 2-cyanoacrylate
n-butyl 2-cyano-3-methoxyacrylate
isobutyl 2-cyano-3-methoxyacrylate
n-butyl 2-cyano-3-phenylacrylate
isobutyl 2-cyano-3-phenylacrylate
n-butyl-2-cyano-2-butenoate
isobutyl-2-cyano-2-butenoate
n-butyl-2-cyano-2-pentenoate
isobutyl-2-cyano-2-pentenoate
n-butyl-2-cyano-2-hexenoate
isobutyl-2-cyano-2-hexenoate
n-butyl-2-cyano-2-heptenoate
isobutyl-2-cyano-2-heptenoate
n-butyl-2-cyano-2-octenoate
isobutyl-2-cyano-2-octenoate
n-butyl-2-cyano-2-nonenoate
isobutyl-2-cyano-2-nonenoate
n-butyl-2-cyano-2-decenoate
isobutyl-2-cyano-2-decenoate
N-propyl-2-cyanoacrylamide
N-butyl-2-cyanoacrylamide
N-pentyl-2-cyanoacrylamide
N-hexyl-2-cyanoacrylamide
N-heptyl-2-cyanoacrylamide
N-octyl-2-cyanoacrylamide
N-nonyl-2-cyanoacrylamide
N-decyl-2-cyanoacrylamide
N-benzyl-2-cyanoacrylamide
N-cyclohexyl-2-cyanoacrylamide
N-ethoxyethyl-2-cyanoacrylamide
N-ethoxypropyl-2-cyanoacrylamide
N-ethoxybutyl-2-cyanoacrylamide
N-ethoxypentyl-2-cyanoacrylamide
N-ethoxyhexyl-2-cyanoacrylamide
N-ethoxyheptyl-2-cyanoacrylamide
N-ethoxyoctyl-2-cyanoacrylamide
N-ethoxynonyl-2-cyanoacrylamide
N-ethoxydecyl-2-cyanoacrylamide
N-propoxyethyl-2-cyanoacrylamide
N-propoxypropyl-2-cyanoacrylamide
N-propoxybutyl-2-cyanoacrylamide
N-propoxypentyl-2-cyanoacrylamide
N-propoxyhexyl-2-cyanoacrylamide
N-propoxyheptyl-2-cyanoacrylamide
N-propoxyoctyl-2-cyanoacrylamide
N-propoxynonyl-2-cyanoacrylamide
N-propoxydecyl-2-cyanoacrylamide
N-butoxyethyl-2-cyanoacrylamide
N-butoxypropyl-2-cyanoacrylamide
N-butoxybutyl-2-cyanoacrylamide
N-butoxypentyl-2-cyanoacrylamide
N-butoxyhexyl-2-cyanoacrylamide
N-butoxyheptyl-2-cyanoacrylamide
N-butoxyoctyl-2-cyanoacrylamide
N-butoxynonyl-2-cyanoacrylamide
N-butoxydecyl-2-cyanoacrylamide Compounds which may prove useful in the practice of the invention include:

n-butyl 2-cyano-3-aminoacrylate
isobutyl 2-cyano-3-aminoacrylate
thio-n-butyl-2-cyanoacrylic acid
thio-isobutyl-2-cyanoacrylic acid
thio-n-propyl-2-cyanoacrylic acid
thio-isopropyl-2-cyanoacrylic acid
thio-n-pentyl-2-cyanoacrylic acid
thio-isopentyl-2-cyanoacrylic acid
1-cyano-2-propenyl butyl sulfoxide
1-cyano-1-propenyl butyl sulfoxide
1-cyano-ethyl butyl sulfoxide
2-cyanoaniline
2-amino-3-cyanotoluene
2,4-diamino-3-cyanotoluene
2-butyl-5-cyano-1,4-benzoquinone
2-cyano-1,4-benzoquinone
2-amino-3-cyano-1,4-benzoquinone
2-butyl-6-cyano-2,5-cyclohexadiene-1-one
5,6-dihydro-2-oxo-2-H-pyran-3-carbonitrile
5-hydro-6-methyl-2-oxo-2-H-pyran-3-carbonitrile
5,6,7-trihydro-2-oxo-3-oxepin-carbonitrile The dosage of a trichogenic composition under the invention required for stimulation of hair growth depends on the species of the subject animal, as well as the age, gender, and overall condition of the subject, and the degree and cause of the alopecia or injury to hair-bearing skin. Dosage also depends on the potency of the active ingredient, its formulation, and mode of application. Consequently, a precise dosage for each type of treatment is not given; instead appropriate dosage can be determined by the experimentalist or caregiver by routine experimentation, for example, using one or more animal systems as described herein. Dosages and associated regimens are routine in the art. This process can be performed for any mammal and, if necessary, for each recipient prior to a full dose application. The composition can be simply applied to the skin surface and need not be rubbed into the skin. In certain situations it may be desirable to apply the composition by spraying it over a larger skin surface. Such a spraying might be a preferable approach to application if the mammals are animals such as sheep, (improved fleece yield), cattle (improved leather), or valuable fur animals such as minks, etc. ...

One approach involves applying a composition which includes a cyanocarboxylic acid derivative and a vehicle for that cyanocarboxylic acid derivative. The ratio of amounts of these can begin with a composition of 0.0001% by weight of cyanocarboxylic acid derivative and 99.999% of the vehicle for that derivative and the results observed over a period of days. Then, the relative percentage by weight of cyanocarboxylic acid derivative versus the vehicle is increased until the desired result within the desired time frame.

In general, an effective dose of topically applied trichogenic composition per unit area of skin depends on the active ingredient and its formulation. In the case of butyl cyanoacrylate, the dose of active ingredient per unit area of skin surface which is effective in stimulating hair growth ranges from about 1 µg cm$^{-2}$ to about 20 mg cm$^{-2}$. More preferably the dose of butyl cyanoacrylate is in the range from about 10 µg cm$^{-2}$ to about 20 mg cm$^{-2}$. Most preferably the dose of butyl cyanoacrylate is in the range from about 5 mg cm$^{-2}$ to about 20 mg cm$^{-2}$.

In other situations it might be preferable to add the composition to shampoo—for animals or even humans. The amount to be added to the shampoo varies depending on the amount of hair growth activity desired. For example, if a significant amount of hair growth is desired the relative amount of the composition would be greater than if the rate of hair growth is to be maintained. The various shampoos would then indicate the level of strength.

C. Experimental

Figure 2:
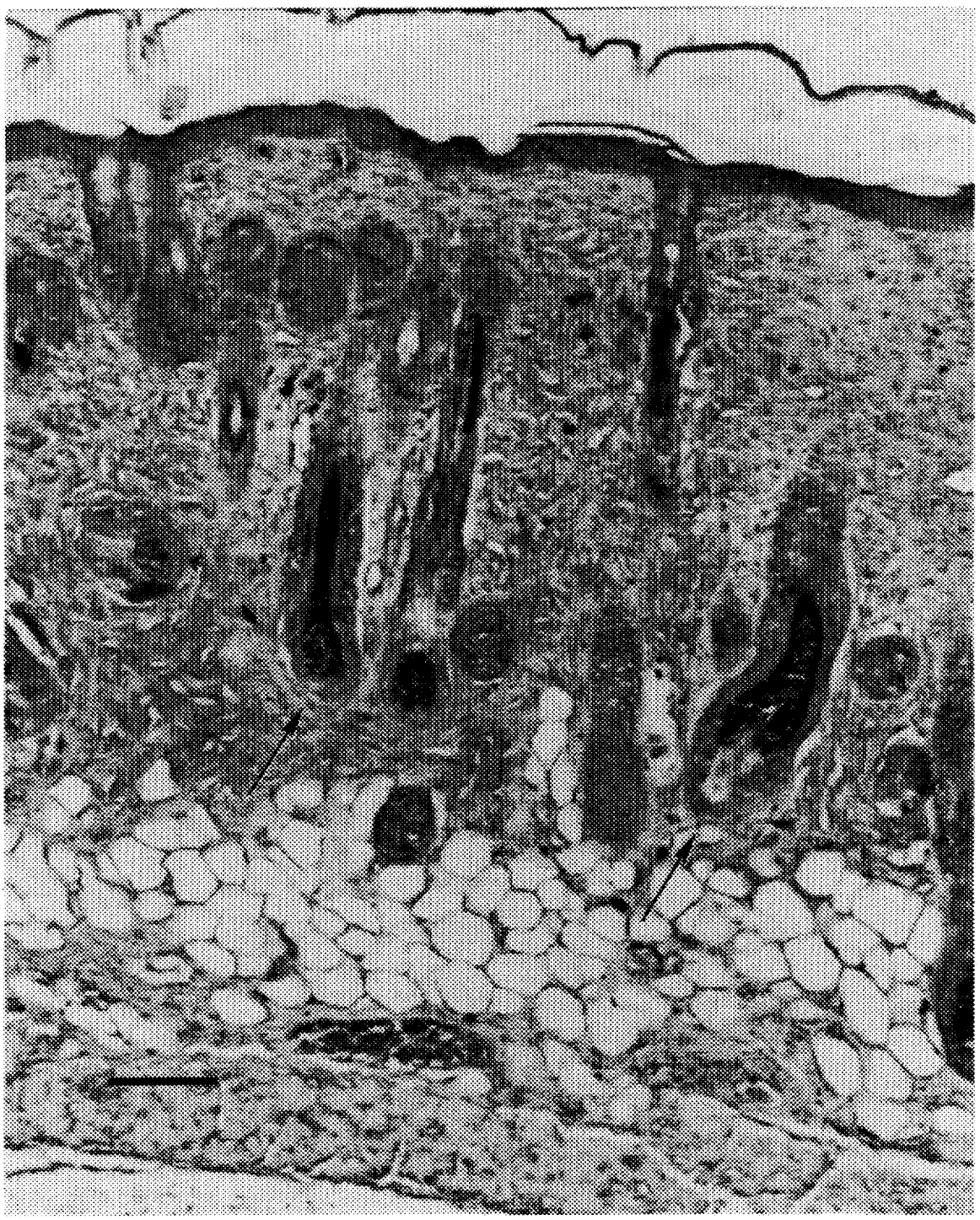
FIG. 2 is a photomicrograph of a skin section of a C57BL/KsJ db/+ mouse 10 days after n-butyl cyanoacrylate application, showing an increase in the number of mature hair follicles. The arrows indicate examples of mature hair follicles. The bar represents 100 $\mu$m.
Figure 3A:
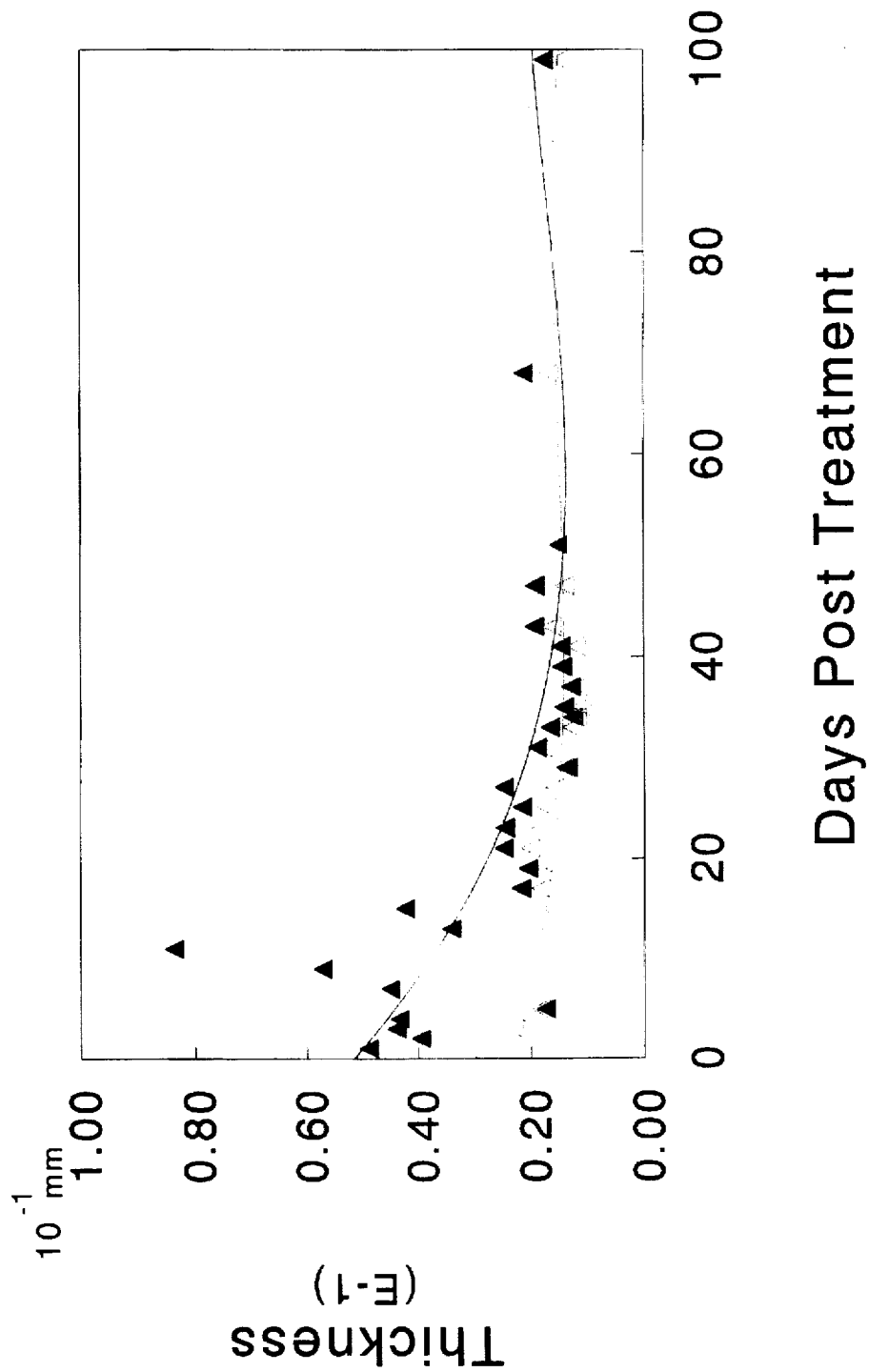
FIG. 3A is a graph comparing the thickness of the epidermis layer between the n-butyl cyanoacrylate-treated and adjacent untreated areas. The maximum increase in thickness in the treated areas (filled triangles) is about 2 fold the maximum level in the untreated areas (open triangles). The epidermis returns to normal thickness at about 40 days post treatment. Each time point represents 2–6 mice of the strain C57BL/KsJ db/+.
Figure 3B:
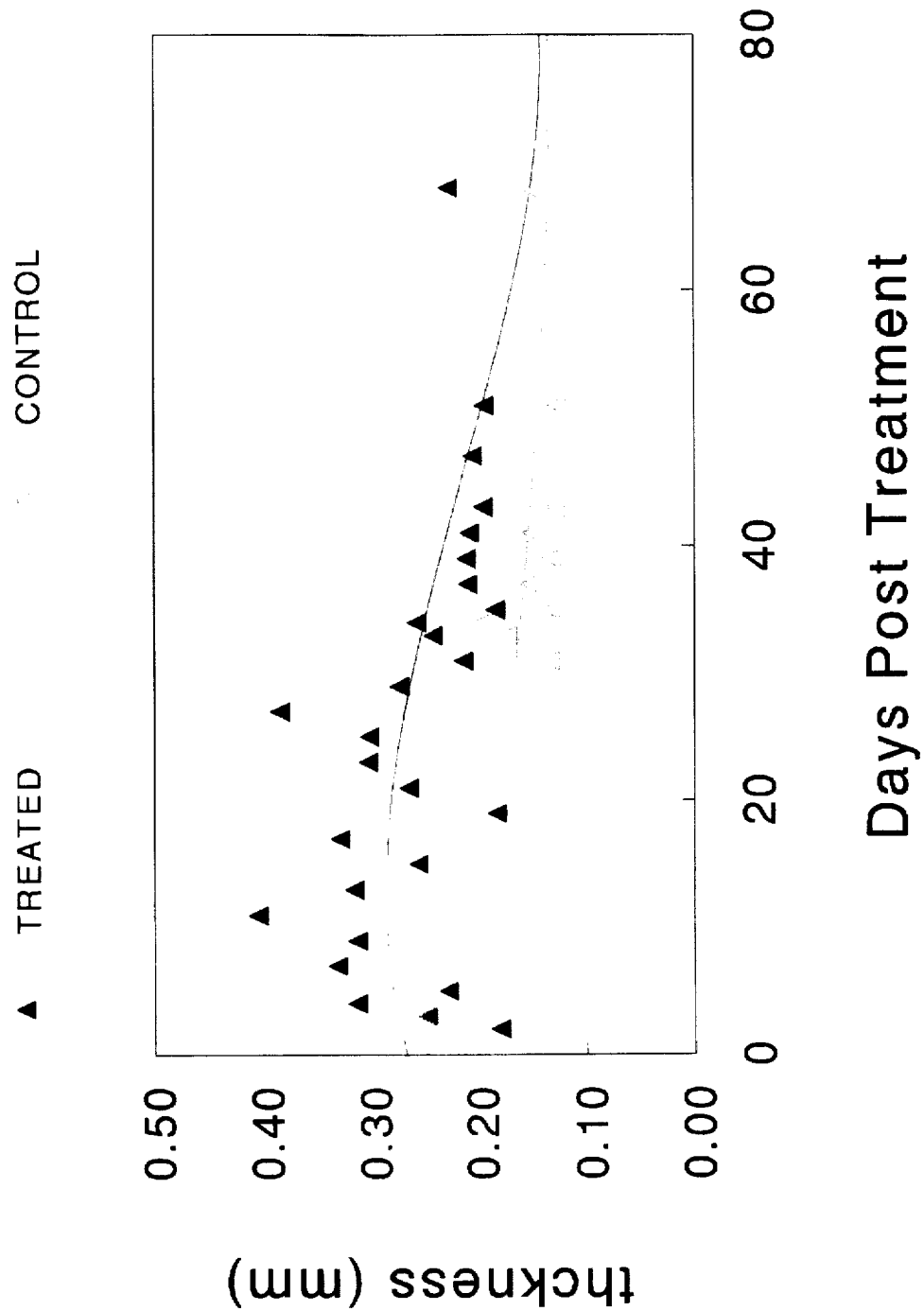
FIG. 3B is a graph comparing the thickness of the dermis layer between the n-butyl cyanoacrylate-treated and the untreated areas. The thickness in the treated areas (filled triangles) is about 1.3 fold that of untreated areas (open triangles) at the first day after treatment, reaches 1.5 fold increase at days 16–20 post treatment, and returns to normal at about 70 days post treatment. Each time point represents 2–6 mice of the strain C57BL/KsJ db/+.
Figure 3C:
FIG. 3C is a photomicrograph of a skin section of a C57BL/KsJ db/+, showing large mature hair follicles traversing the entire thickness of the skin 16 days following application of n-butyl cyanoacrylate. The arrows indicate examples of large mature hair follicles. The bar represents 100 $\mu$m.
Figure 4A:
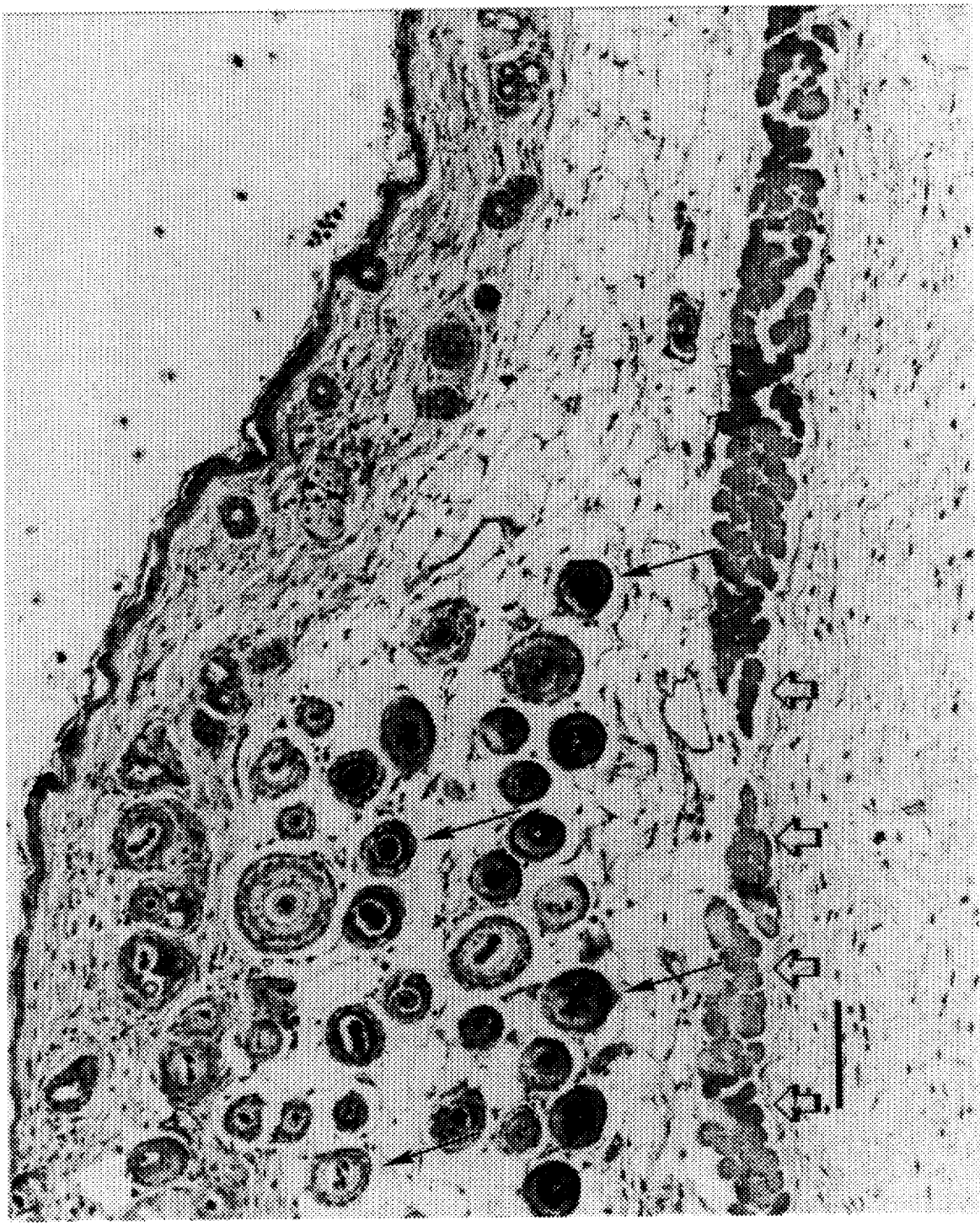
FIG. 4A is a photomicrograph of a skin section of a C57BL/KsJ db/+ mouse at 19 days after the left side was treated topically with n-butyl cyanoacrylate (big arrows). A high concentration of large mature hair follicles (cut in cross-section and indicated by the small arrows) occupies much of the subcutaneous space in the treated area. However the adjacent untreated area has few hair follicles in the subcutaneous space. There is a clear boundary between the treated and untreated areas in terms of hair follicle number and the thickness of the skin. The bar represents 100 $\mu$m.
Figure 4B:
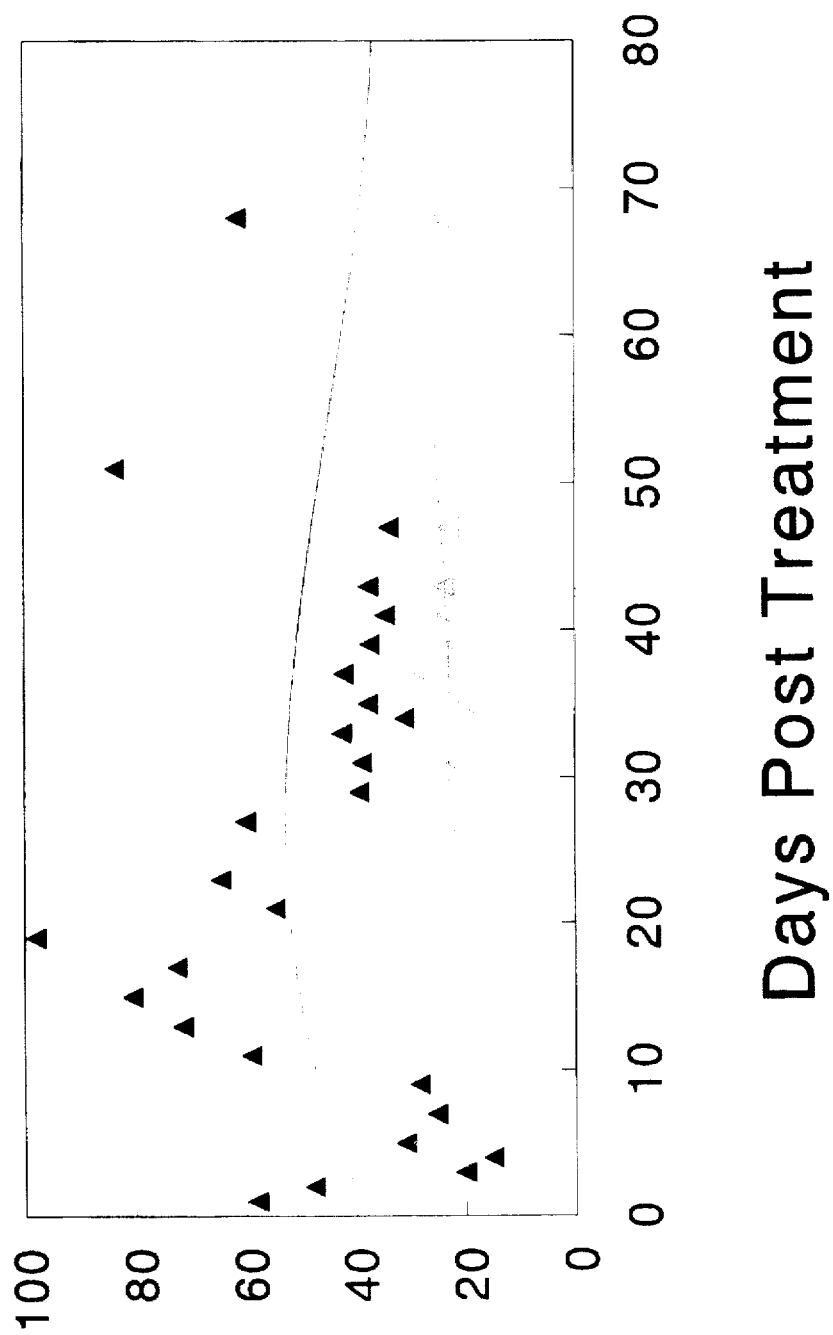
FIG. 4B is a graph comparing the hair follicle number between the n-butyl cyanoacrylate-treated (filled triangles) and adjacent untreated skin (open triangles). In the strain C57BL/KsJ db/+, the maximum increase in the number of hair follicles in the treated areas is about 2 fold that of untreated areas. Each time point represents 2–6 mice.

C.1 Cutaneous Changes Associated with the Application of a Trichogenic Composition Comprising n-Butyl Cyanoacrylate The dorsal aspect of C57BL/KsJ db/+ female mice was shaved and a single topical dose of n-butyl cyanoacrylate (formulated as Nexaband® Liquid) was applied. Within six hours of application a slight thickening of the treated skin was observed. The response correlates temporally with inflammation in the dermis and subcutaneous layer; the keratin becomes irregular and the epithelial layer shows signs of intermittent disruption; inflammatory cell infiltrate can be seen in the dermis, and new aggregates of cells are found in the subcutaneous layer. At this early stage some of these new aggregates form laminae and appear to constitute neo-angiogenesis. At day 1 post application, the gross appearance of inflammation was still apparent, and there was microscopic evidence for the formation of a lumen from an aggregate of cells in the subcutaneous layer. At day 2 post application, an aggregate of cells constituting a lumen in the subcutaneous layer was shown to be positive for vimentin (indicating mesenchymally derived cells). At day 3 post application, evidence of trichogenesis was clearly seen at the treatment site: the epidermis was multilayered and multiple complex epidermal projections appeared to constitute hair follicle anlage (FIG. 1). These changes were only observed in the treated area. At day 10 post application, microscopic observation showed that the new epithelial pegs had developed into mature hair follicles (in anagen (active) phase) (FIG. 2). Between eight and 12 days post application, hair follicles and new hair were present at the sites of application; the remainder of the shaved area remained hairless. Epidermal and dermal thickening and new hair follicle development in treated skin were pronounced until days 10–20 post application (FIGS. 3A–3B), at which time large mature hair follicles traversed the entire thickness of the dermis and subcutaneous layer (FIG. 3C). Hair follicle density reached a maximum level at about days 20–30 post application, at which time the epithelium and connective tissue elements began to return to their pre-treatment appearance (FIGS. 4A–4B).

Figure 6A:
FIG. 6A is a photograph of the dorsal aspect of a diabetic C57BL/KsJ db/db mouse taken 27 days post application of n-butyl cyanoacrylate. The hair growth appears in a rectangle pattern with three hair growth dots above the rectangle (arrows), exactly along the pattern of the application. The untreated adjacent skin remained hairless.
Figure 6C:
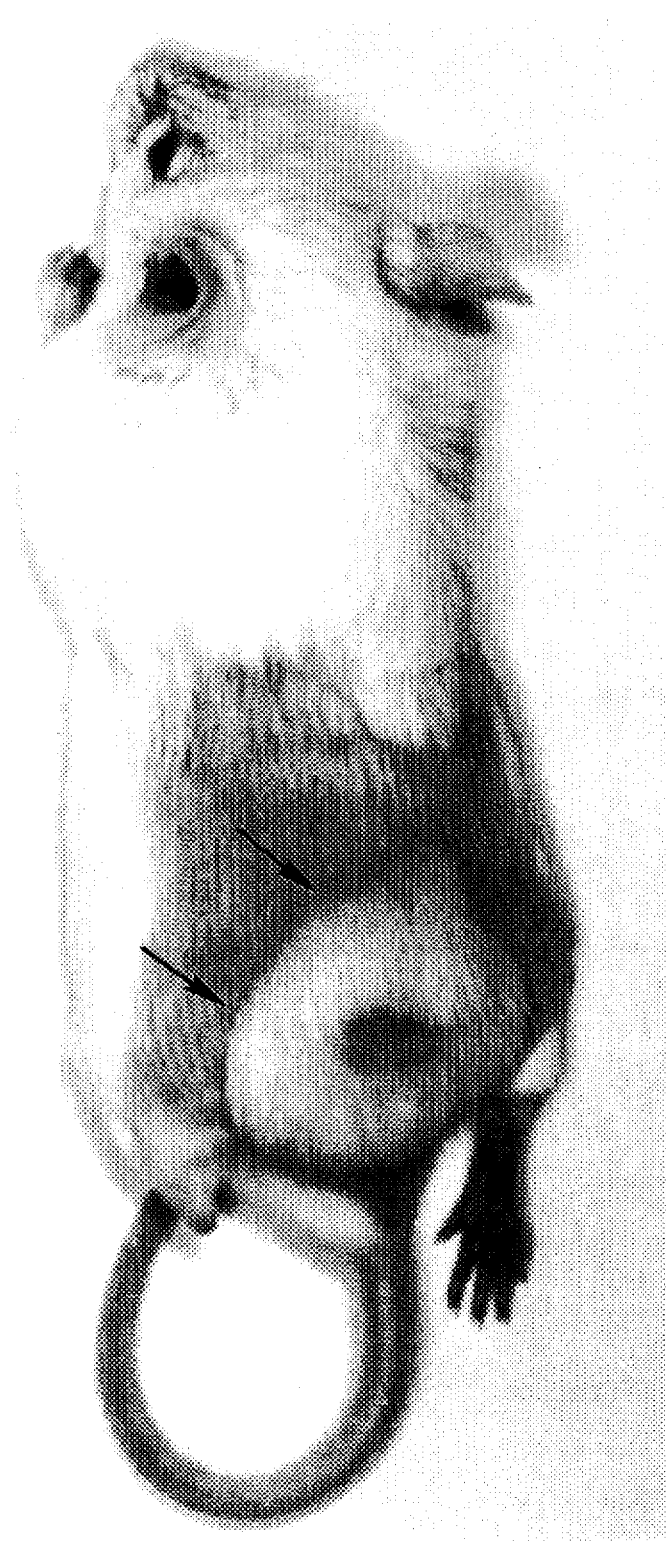
FIG. 6C is a photograph of the dorsal aspect of a Balb/cBYj nu/+ mouse taken 19 days post application of n-butyl cyanoacrylate. The hair growth appears in a circle pattern (arrows), exactly along the pattern of the application. The untreated adjacent area remained hairless.
Figure 7A:
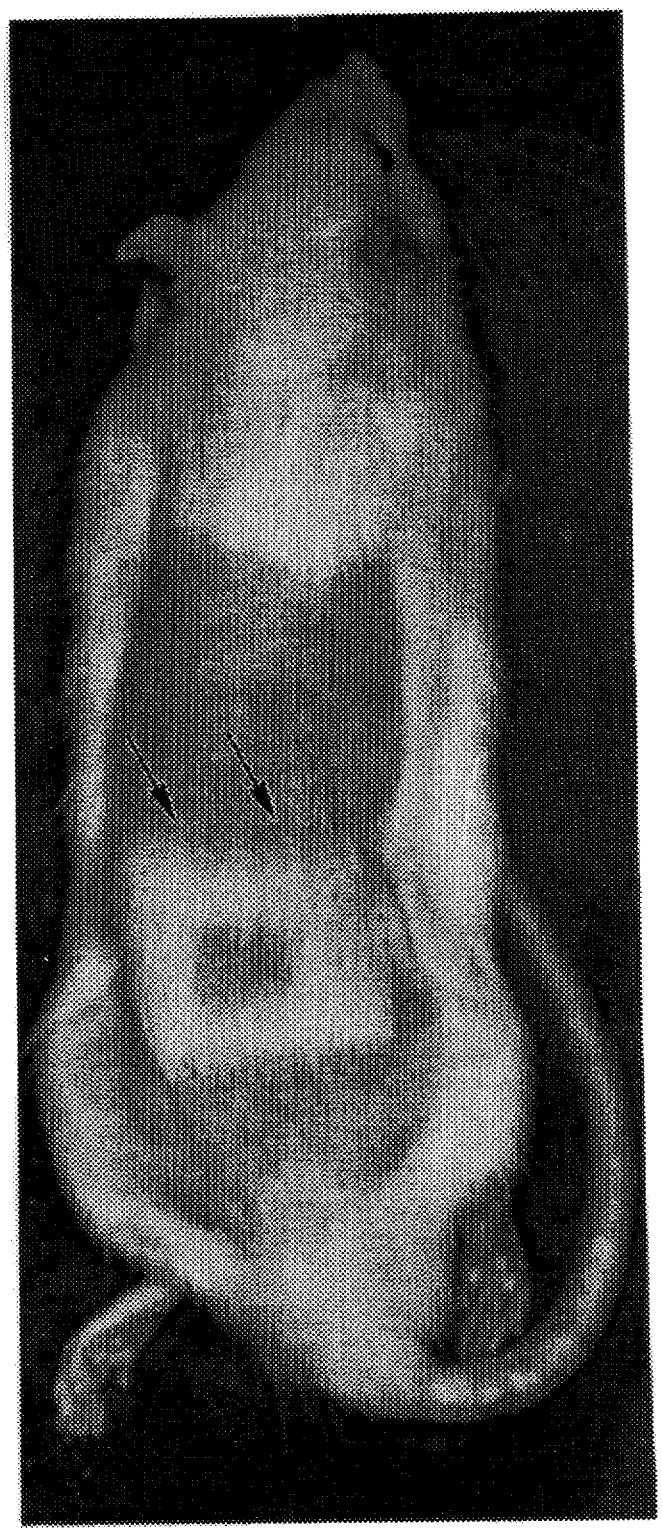
FIG. 7A is a photograph of the dorsal aspect of a Sprague Dawley rat taken 23 days post application of n-butyl cyanoacrylate. The hair growth appears as a rectangle pattern (arrows) exactly along the pattern of the application. The untreated adjacent area remained hairless.
Figure 7B:
FIG. 7B is a photomicrograph of a skin section of a Sprague Dawley rat, showing a much higher density of hair follicles in treated area (big arrows) compared to the untreated area. There is a boundary between the treated and untreated areas in terms of hair follicle number. The small arrows indicate examples of hair follicles. The bar represents 400 μm.

At the gross level, the hair growth in the shaved treated area occurs at 8–12 days and reaches full length at about 14–20 days post treatment, however, the remainder of the shaved untreated area remains hairless and the hair follicles small (in telogen (resting) phase) (5A–5B). The response of hair growth to the n-butyl cyanoacrylate stimulus is very similar in 6 other strains of mice (C57BL/KsJ+/+, C57BL/KsJ db/db, Balb/cBYj+/+, Balb/cBYj nu/+, HRS/J hr/+, and RHJ/LeJ hr$^{rh-j}$/+) (FIGS. 6A–6C) and Sprague Dawley rats (FIGS. 7A–7B). The hair growth rate in the fastest growth period (at about 10–15 days post treatment) reaches 1 mm per day. This is entirely consistent with the microscopically observed stimulation of hair follicles following treatment.

The evidence at both micro- and macro-levels demonstrates that the net effect of the treatment of skin with n-butyl cyanoacrylates is induction of de novo development of new hair follicles and a shift in the hair growth cycle from telogen to anagen.

C.2 Induction of Hair Follicles by Subdermal Application of n-Butyl Cyanoacrylate in vivo.

The effect of n-butyl cyanoacrylate on the dermis is shown as follows. An incisional, full-thickness wound, about 2 cm long was made through the dorsal skin of five mice (strain C57BL/KsJ db/+). A single dose of about 10 mg of n-butyl cyanoacrylate (in 10 µl of Nexaband® Liquid) was applied to the bottom of the wound, and the wound closed with two surgical clips. Control animals which received 10 µl of phosphate buffered saline (PBS: 0.144 g/l $KH_2PO_4$, 9.0 g/l NaCl, 0.795 g/l $Na_2HPO_4.7H_2O$; pH 7.2) were processed identically. During the period of 1–90 days post application, the effect of n-butyl cyanoacrylate treatment was examined by macroscopic observation. Histological effects were observed by folliculogram: skin samples containing treated and untreated areas were harvested, fixed in 10% buffered formalin, embedded in paraffin, sectioned at 5 µm, and stained with Hematoxylin & Eosin or Masson trichrome in preparation for microscopic examination.

In a group of five C57BL/KsJ db/+ mice, a full-thickness excisional wound was made with a biopunch (6 mm diameter) on the dorsal skin. A single dose of 9 mg of n-butyl cyanoacrylate (in 10 µl of Nexaband® Liquid) was applied to the bottom of the wound, and the wound was left open. Control animals which received 10 µl of PBS were treated identically.

In another example, 20 µl of n-butyl cyanoacrylate was applied subdermally by subcutaneous injection to a group of C57BL/KsJ db/+ mice.

Figure 8A:
FIG. 8A is a photograph of dorsal aspect of C57BL/KsJ db/+ mouse with an incision wound treated with n-butyl cyanoacrylate, showing profound hair growth along the linear wound margin (arrow) at day 17 post treatment.
Figure 8B:
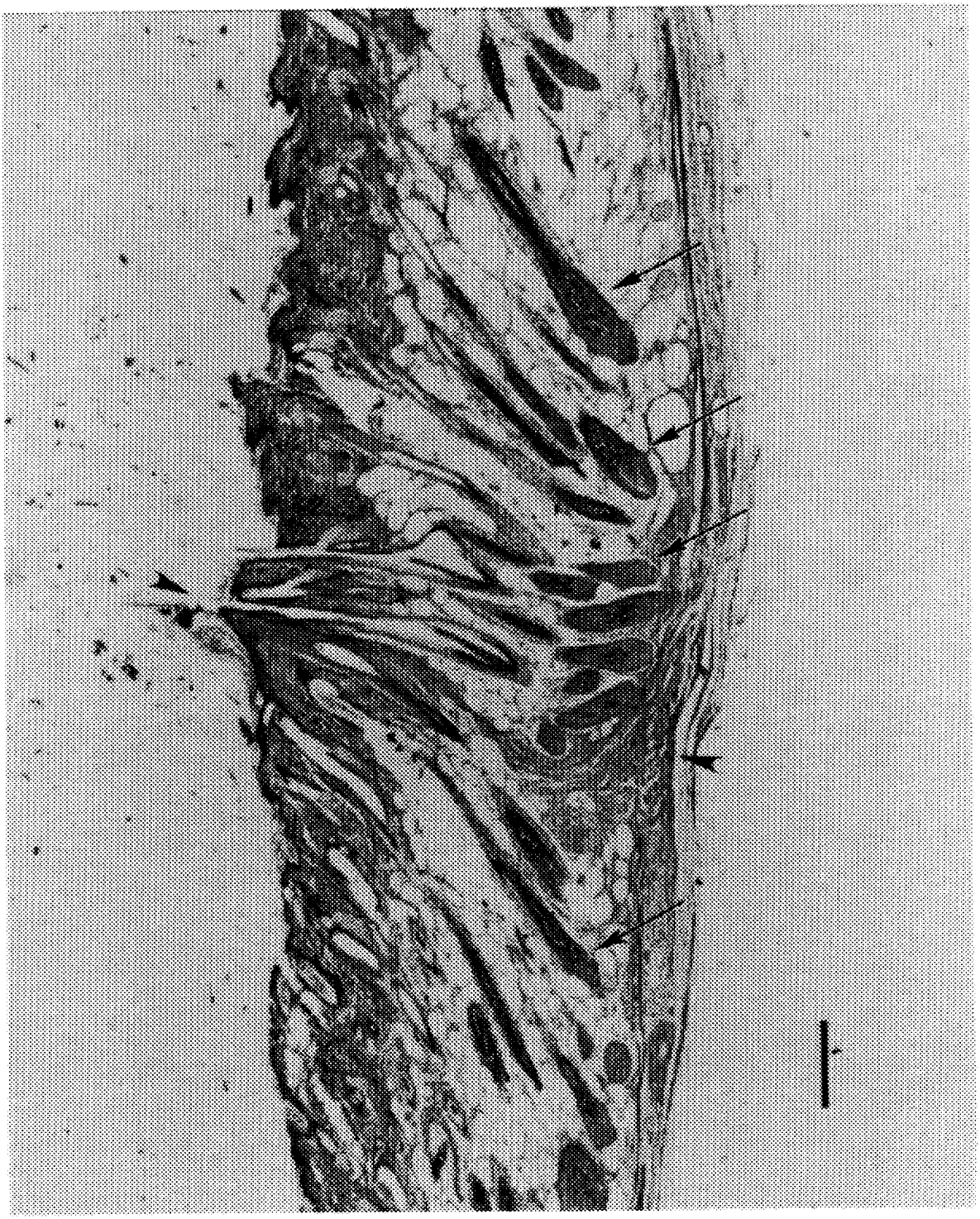
FIG. 8B is a photomicrograph of an incisional wound to which n-butyl cyanoacrylate was applied, showing the development of many new hair follicles and little scar tissue in the wound site (between the big arrows) at day 17 post treatment. There are fewer and smaller hair follicles farther from the wound site, indicating that the process of remodelling and normalizing of the wound was accelerated. The small arrows indicate examples of hair follicles. The bar represents 200 μm.
Figure 8C:
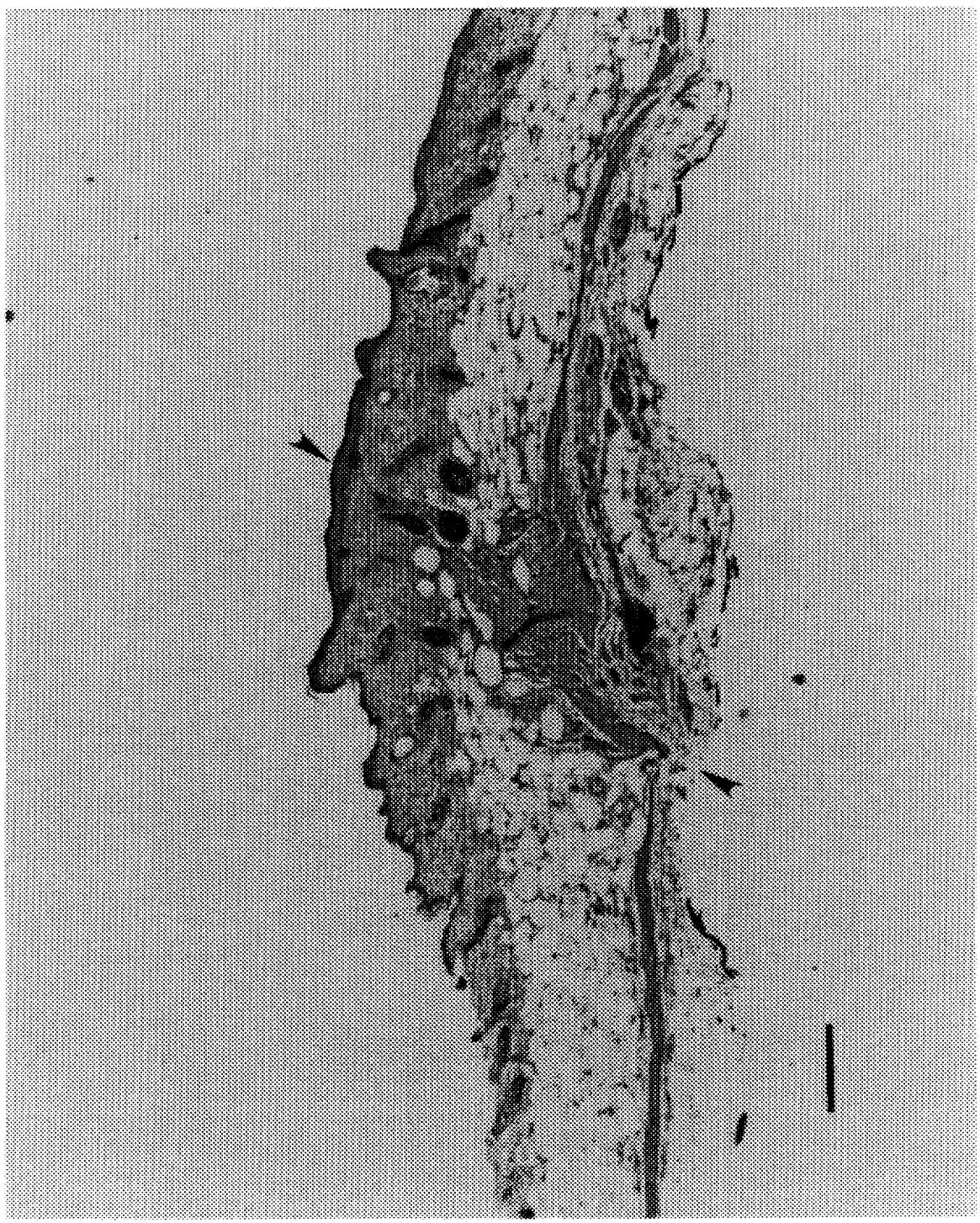
FIG. 8C is a photomicrograph of skin section of a C57BL/KsJ db/+ mouse, showing few hair follicles but plenty of scar tissue in the incisional wound site (between the big arrows) at day 17 post treatment with PBS, a control for FIG. 8B. The bar represents 200 μm.
Figure 9:
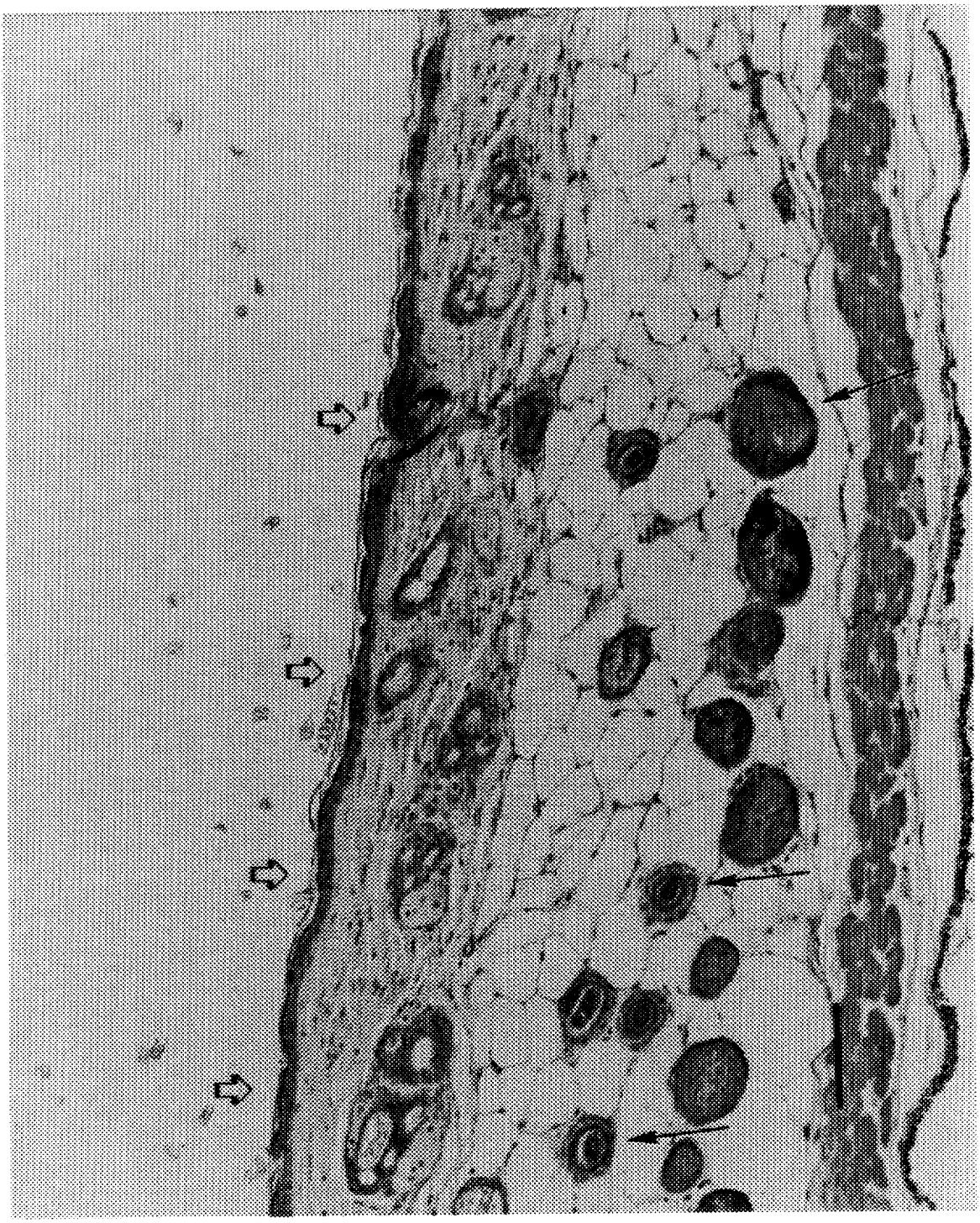
FIG. 9 is a photomicrograph of skin section of a C57BL/KsJ db/+ mouse, showing the development of new hair follicles in the treated site (big arrows) and few hair follicles in the untreated site 68 days after subcutaneous injection with n-butyl cyanoacrylate. The small arrows indicate examples of hair follicles in the dermis. The bar represents 100 μm.

Application of n-butyl cyanoacrylate to incisional and excisional wounds stimulated hair growth along the wound margin (FIGS. 8A–8C). Moreover, microscopic examination revealed that subdermal treatment by application to a full thickness incisional or excisional wound induced de novo hair follicle formation in the subcutaneous adipose layer, in the dermis, as well as in the wound site (FIG. 8B). In each case, new hair follicles subsequently grow in the wound site through what would normally be scar devoid of skin appendages as shown in FIG. 8C, indicating an additional advantage is that the de novo hair follicle development in wound site accelerates the process of wound remodelling (normalizing). The direct delivery of n-butyl cyanoacrylate into subcutaneous layer by subcutaneous injection also induces de novo hair follicle formation and the thickening of full-thickness skin, compared to the untreated site (FIG. 9). In the above three cases, the phenomenon that the farther the distance from the treated site is, the fewer and the smaller the hair follicles are, again demonstrating the localized nature of the effect of n-butyl cyanoacrylate on hair growth.

C.3 The Stimulation of Hair Growth by n-Butyl Cyanoacrylate in Mice Previously Treated with Cyclophosphamide and Doxorubicin The induction of hair loss following treatment with certain anticancer drugs, such as cyclophosphamide or doxorubicin, is well documented (A. Tierney & J. Taylor (1991) Nurs. Stand 5:29–31; R. R. Love, et al. (1989) Cancer 63:604–612; B. W. Cline (1984) Cancer Nurs. 7:221–228). The following experiment was performed to determine the effect of n-butyl cyanoacrylate on hair regrowth in mice pre-treated with cyclophosphamide or doxorubicin. Twenty mice of strain C57BL/KsJ db/+ were peritoneally injected with either cyclophosphamide in PBS (20 mg per kilogram of body weight) or Doxorubicin in PBS (2 mg per kilogram of body weight) for 10 consecutive days. Then a single 10 µl dose of n-butyl cyanoacrylate was applied topically to an area of the shaved dorsum of each animal. Control mice, which were injected with PBS alone, were treated similarly. The effects of hair regrowth were determined both by phototrichogram (macroscopic observation using photography) and by folliculogram (microscopic observation of histological changes in the treated and untreated skin).

Figure 10A:
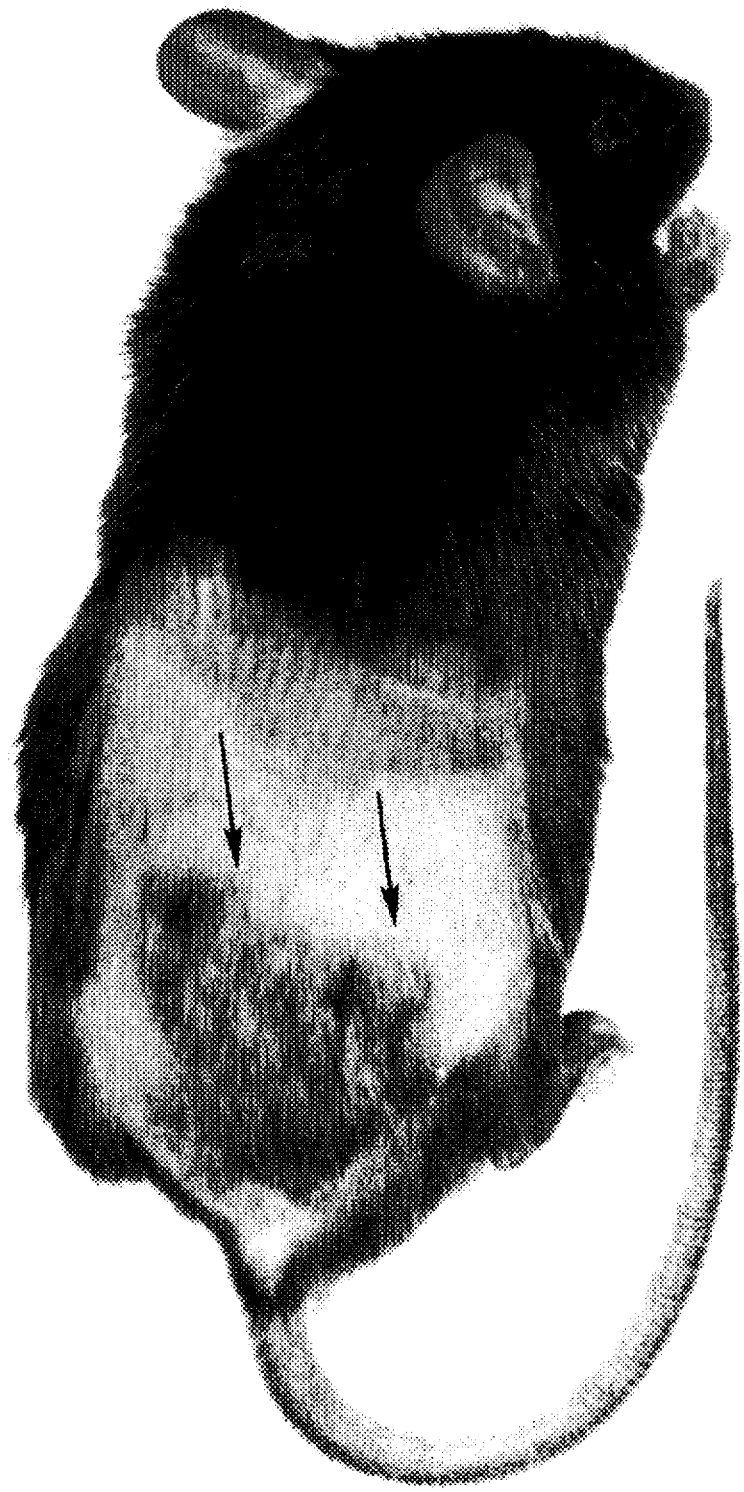
FIG. 10A is a photograph of the dorsal aspect of a C57BL/KsJ db/+ mouse (pre-treated with cyclophosphamide) taken 31 days post application of n-butyl cyanoacrylate. There is a profound growth of new unpigmented gray hairs in the treated area (arrows). The adjacent untreated skin is hairless and shows a lack of pigmentation.
Figure 10B:
FIG. 10B is a photograph of the dorsal aspect of a C57BL/KsJ db/+ mouse (pre-treated with doxorubicin) taken 31 days post application of n-butyl cyanoacrylate. There is a profound growth of hair with normal pigmentation in the treated area (arrows). The untreated skin is hairless and has normal pigmentation.
Figure 10C:
FIG. 10C is a photograph of the dorsal aspect of a C57BL/KsJ db/+ mouse (pre-treated with cyclophosphamide) taken 202 days post application of n-butyl cyanoacrylate, showing the lack of pigmentation in the new growth hairs in treated area (arrows).

All mice pre-treated with cyclophosphamide, doxorubicin and PBS showed rapid hair regrowth in the areas where n-butyl cyanoacrylate was applied: beginning at 8–11 days and growing to full length at 15–18 days post treatment with n-butyl cyanoacrylate. In contrast, in the adjacent skin not treated with n-butyl cyanoacrylate in the groups pre-treated with cyclophosphamide or doxorubicin, hair regrowth did not occur until 80 days after the beginning of the experiment (FIGS. 10A–10B). In the animals pre-treated with cyclophosphamide, lack of pigmentation was observed in the new hair growth as well as in the skin of the untreated hairless area. The new hair occurred only in the areas treated with n-butyl cyanoacrylate and remained until the mice were sacrificed 335 days after treatment with n-butyl cyanoacrylate (FIG. 10C). This is a good indicator that the hairs induced by n-butyl cyanoacrylate are persistent and join into the last pelage. Thus the dual treatment with cyclophosphamide and n-butyl cyanoacrylate together can be used to study the mechanism of the melanogenesis metabolism, the prevention and the treatment of various diseases of abnormal pigmentation metabolism.

C.4 The Effect of n-Butyl Cyanoacrylate Treatment on Hair Growth in ex vivo

The studies on induction of hair follicle or elongation of hair shaft with organ culture methods are well documented (R. F. Oliver (1970) J. Embryol. Exp. Morphol. 23:219–236; C. A. B. Jahoda (1992) Development 115:1103–1109; C. A. B. Jahoda & A. J. Reynolds (1993) J. Investg. Dermatol. 101:33S-38S). In those studies, the elongation of the hair shaft is too short and required microscopic observation. The following experiment was performed to determine how strong the effect of n-butyl cyanoacrylate on hair growth was in the condition of organ culture and if the hair growth was visible.

Figure 11:
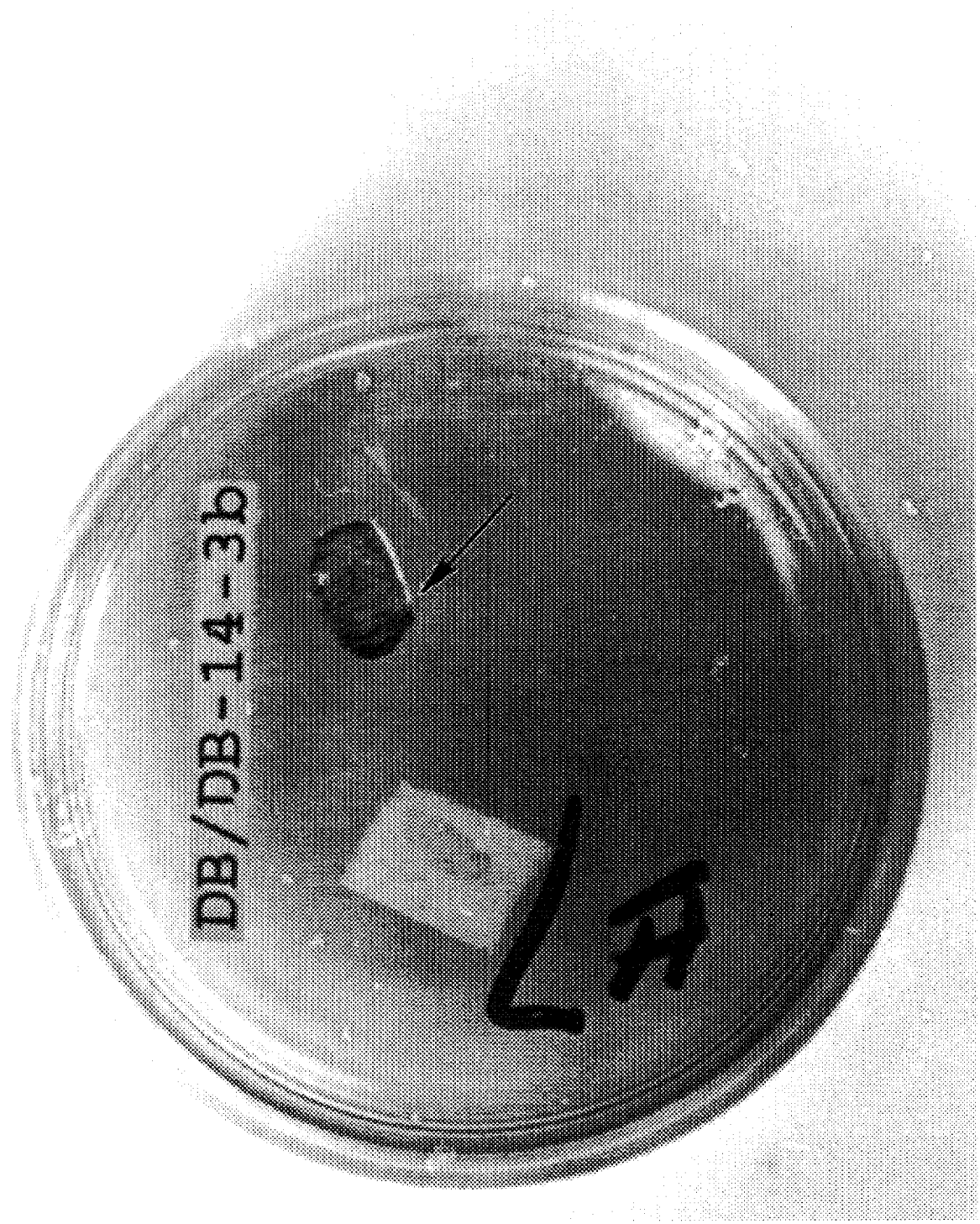

The shaved dorsal skin of mice (C57BL/KsJ db/+ and C57BL/KsJ db/db) was treated with n-butyl cyanoacrylate by a single topical application at a dose of 10 mg cm$^{-2}$. One hour later, the skin (0.5×1.0 cm) containing both treated and untreated areas was excised, rinsed in PBS, cultured in Dulbecco's Modified Eagle Medium (Gibco BRL, Gaithersburg, Md.) supplemented with 10% fetal bovine serum (HyClone Laboratories, Logan, Utah) at an atmosphere of 95% $O_2$ and 5% $CO_2$, 37° C. Hair growth was recorded by macroscopy. Hair growth in the treated area was observed at days 7–12 post treatment and lasted to the end of the experiment (at day 25 post treatment); the untreated area remained hairless (FIG. 11).

C.5 The Effect of n-Butyl Cyanoacrylate Treatment on Growth Factor Activity in Skin Extracts A single topical application of 20 mg of n-butyl cyanoacrylate was made to an area of shaved skin on the dorsum of strain C57BL/KsJ db/+ mice. At days 10 and 20 post-treatment, skin samples were excised from treated areas. Skin tissue was frozen in dry ice, minced, homogenized in ice-cold PBS, and centrifuged at 15,000 g for 30 minutes at 4° C. The protein concentration of supernatants was adjusted to 1.0 mg/ml by the BioRad assay procedure (BioRad Laboratories, Richmond, Calif.). Skin samples from untreated areas of the same strain were harvested and processed identically. Mouse serum albumin was prepared at a concentration of 1.0 mg/ml in PBS as a control. An aliquot of each supernatant extract was fractionated according to size with a nominal 30 kilo Dalton (kDa) cutoff, and the low molecular weight fraction ($\leq 30$ kDa) was included in the fibroblast cell proliferation assay, as follows.

The supernatant extracts from treated and untreated skin samples, and mouse serum albumin control, were added to a quartet of wells in a 96 well plate, and 2-fold serially diluted 11 times. NIH/3T3 fibroblasts (ex American Type Culture Collection, Rockville, Md.) were harvested at about 80% confluence, seeded into each well at a density of 5,000 cells per well, and supplemented with serum-free assay medium (QBSF 56, Quality Biological Inc., Gaithersburg, Md.). Cell proliferation was determined according to the protocol of the CellTitre 96 Non-Radioactive Cell Proliferation Assay (Promega, Madison, Wis.). The results (FIGS. 12A–12B) indicated that protein extracts of treated skin were more active in stimulating proliferation of NIH/3T3 cells, as compared with the protein extract of untreated skin. The extract from skin harvested at 20 days post-treatment was more active than the extract from skin harvested at 10 days post-treatment. In contrast, the low molecular weight fraction of both treated and untreated skin, comprising proteins of 30 KDa or less, showed no discernible effect on cell proliferation. This indicates that component(s) of treated skin which are active in the cell proliferation assay have molecular weights in excess of 30 KDa. The control protein preparation of mouse serum albumin showed no effect on NIH/3T3 cell proliferation.

C.6 The Relationship between the Dose of n-Butyl Cyanoacrylate and the Response of Hair Growth The effect of n-butyl cyanoacrylate concentration on stimulation of hair growth was investigated as follows. Five mice of each of strains C57BL/KsJ db/+ and C57BL/KsJ db/db were shaved on the dorsum, treated with a single topical application of either undiluted Nexaband® Liquid (containing about 10 mg of n-butyl cyanoacrylate per 10 µl), or Nexaband® Liquid diluted to 50% or 25% with vegetable oil. Hair growth was macroscopically scored at 49, 61 and 86 days after treatment. All animals treated with undiluted Nexaband® Liquid were rated at the maximum score at all three time points. Nexaband® Liquid diluted by 50% was less effective in stimulating hair growth than undiluted Nexaband®, while a 25% dilution was even less effective (Table 1). However, hair growth in the area treated with a 25% dilution was still much greater than in the adjacent untreated area, thereby demonstrating that the effect of the invention on stimulating hair growth is dose-dependent, i.e., adjustable in practical use.

TABLE 1

Effect of Various Concentrations of n-Butyl Cyanoacrylate on Hair growth
Number of Animals Exhibiting Hair Growth*

| | | Score: | | | | | | | | | | |
|---|---|---|---|---|---|---|---|---|---|---|---|---|
| | | 49 | | | | 61 | | | | 86 | | | |
| Concentration | Strain | 0 | 1+ | 2+ | 3+ | 0 | 1+ | 2+ | 3+ | 0 | 1+ | 2+ | 3+ |
| 25% | db/+[1] | 4 | 1 | | | 2 | 3 | | | 3 | 2 | | |
| | db/db[2] | 2 | | 2 | 1 | 2 | 1 | 1 | 1 | | | 3 | 2 |
| 50% | db/db[2] | | | 2 | 3 | | | 1 | 4 | | | 2 | 3 |
| 100%[3] | db/+[1] | | | | 5 | | | | 5 | | | | 5 |
| | db/db[2] | | | | 5 | | | | 5 | | | | 5 |

*The scoring scale used is: 0, no obvious hair growth; 1+, mild hair regeneration in an area defined as less than 10% of the treated area; 2+, moderate hair regeneration in an area larger than 10% but less than 50% of the treated area; 3+, high hair regeneration with an area larger than 50% of treated area. [1], C57BL/KsJ db/+ mice; [2], C57BL/KsJ db/db mice; [3], 10 mg/10 µl of n-butyl cyanoacrylate.

C.7 Influence of n-Butyl Cyanoacrylate on Concentration & Localization of Growth Factors in Skin.

Forty stock female mice of strain C57BL/KsJ db/+ at eight weeks of age were treated with a single dose of n-butyl cyanoacrylate applied topically to the shaved dorsum. Animals were sacrificed at days 4, 6, 8, 10, 12, 14, 16, 18, 20, and 22 post-treatment, and skin samples were excised to yield an area of n-butyl cyanoacrylate treated skin together with a contiguous, adjacent sample of untreated skin. In preparation for immunohistochemistry, samples were washed in PBS, fixed in 10% formalin, and secondarily fixed in Bouin's solution prior to paraffin embedding. Multiple 4–5 µm sections were placed on slides pre-coated with 3-aminopropylethoxysilane.

Antibody detection staining was performed using the avidin/biotin peroxidase complex method (J. M. Elias, M. Margiotta, & D. Gabore (1989) *J. Am. Clin. Pathol.* 92:62). The following primary antibodies were used: anti-TGF-β1 neutralizing antibody; anti-TGF-β2,3; and anti-EGF receptor.

Figure 13:
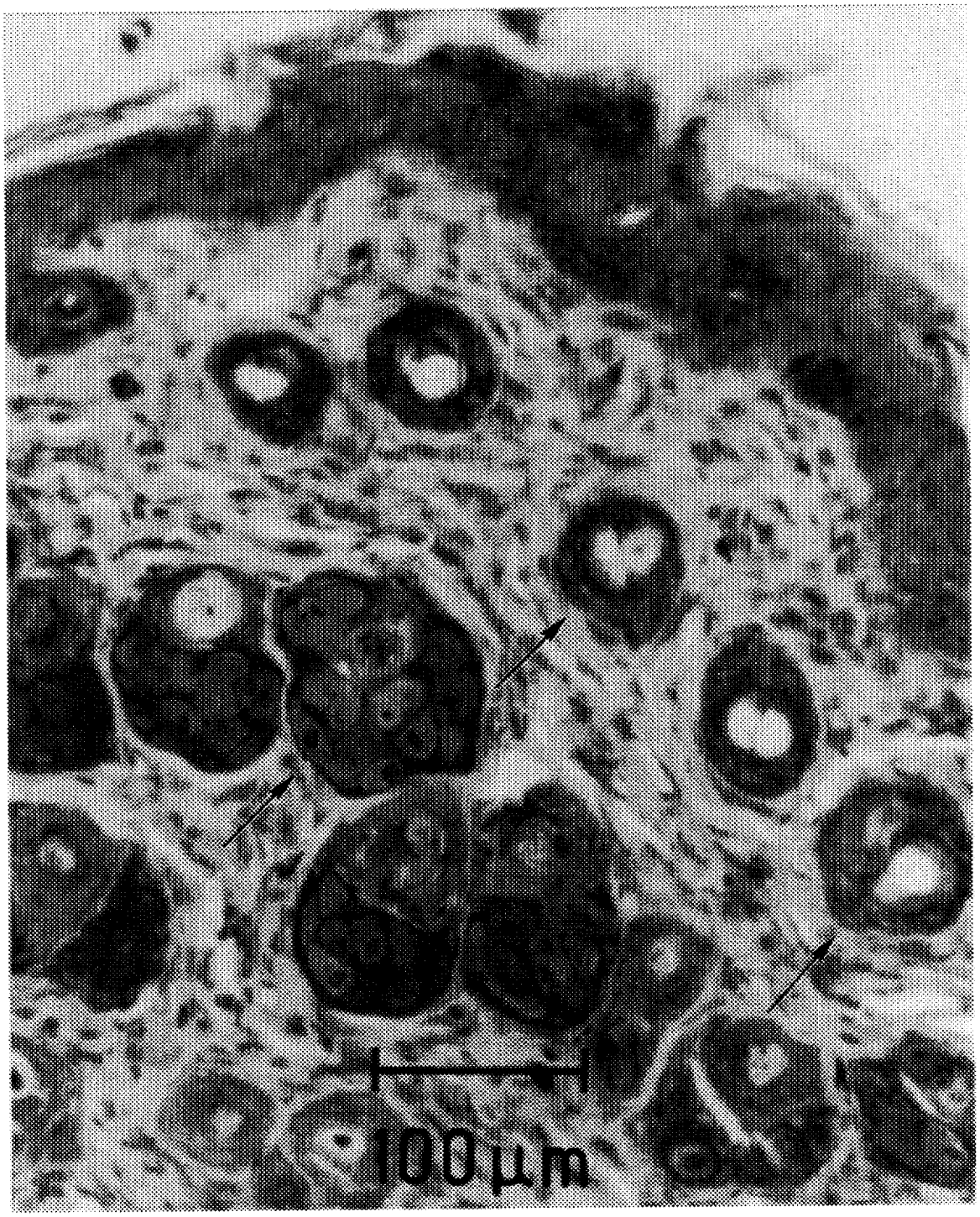
FIG. 13 is a photomicrograph of a skin section stained with anti-TGF-β1 antibody 6 days after treatment with n-butyl cyanoacrylate, showing localization of TGF-β1 in sebaceous glands, epithelial cells and hair follicles in the treated area. The small arrow indicates examples of the stain in sebaceous glands and hair follicles. Bar represents 100 μm.

Localization of the various growth factors was observed as follows: The overall staining pattern for the presence of TGF-β1 in skin tissue treated topically with n-butyl cyanoacrylate is shown in FIG. 13. Skin treated with n-butyl cyanoacrylate showed a specific spatial and temporal distribution of TGF-β1. TGF-β1 was detected in the sebaceous glands, the epithelial cells of the epidermis, hair follicles, and connective tissues (FIGS. 1A–1B). The intensity of staining for TGF-β1 reached a maximum at day 4 and declined to a relatively low level by day 15 post-treatment. This distribution pattern for TGF-β1 implicates TGF-β1 in the differentiation and development of new hair follicles, and indicates its involvement in regulating the hair growth process. TGF-β1 staining was more intense in connective tissue subjacent to treated skin, as compared with untreated skin. A difference in TGF-β1 distribution was observed between developing and mature hair follicles: staining was fairly uniform throughout epithelial cells of developing follicles, but appears to be confined to the outer root sheath in mature follicles.

The distribution of TGF-β2,3 and EGF in treated and untreated skin tissues was similar to that for TGF-β1. However, the intensity of TGF-β2,3 stain in the epidermis was greater than that of TGF-β1 throughout the study period. In connective tissue from treatment areas, much less staining activity of EGF-receptor was found as compared with TGF-β1.

C.8 The Inhibition of n-Butyl Cyanoacrylate-Stimulated Hair Growth by Treatment with Anti-TGF-β1-Neutralizing Antibody Forty mice of strain C57BL/KsJ db/+ eight weeks old were divided into four equal groups (A–D). The dorsal aspect of the mice were shaved, and five different sites on the dorsum were designated (sites 1–5). Each site was 5–6 mm². Animals of group A were treated topically at sites 1, 2 & 3 with n-butyl cyanoacrylate only (10 µl per site) formulated as Nexaband® Liquid. Animals of group B were treated topically at sites 1, 2 & 3 with the same dose of n-butyl cyanoacrylate, but sites 1 and 3 subsequently received subcutaneous injections of either anti-TGF-β1 neutralizing antibody (1 µg per g of body weight) in PBS/0.1% BSA (at site 1), or PBS/0.1% BSA as a matched control (at site 3). Group C animals were treated as for Group B except that anti-EGF neutralizing antibody was injected at site 1 instead of anti-TGF-β1. In all groups, site 4 was a shaved area of skin that did not receive any treatment, while site 5 was an area of normal skin that remained unshaved and received no treatment. Group D animals were shaved only and received no treatment.

Hair regeneration was documented by macroscopic observations supported by serial photographs of treatment sites. Histological observations were made on skin biopsies taken at frequent intervals ranging from 6 hours to 21 days post-treatment.

Figure 14:
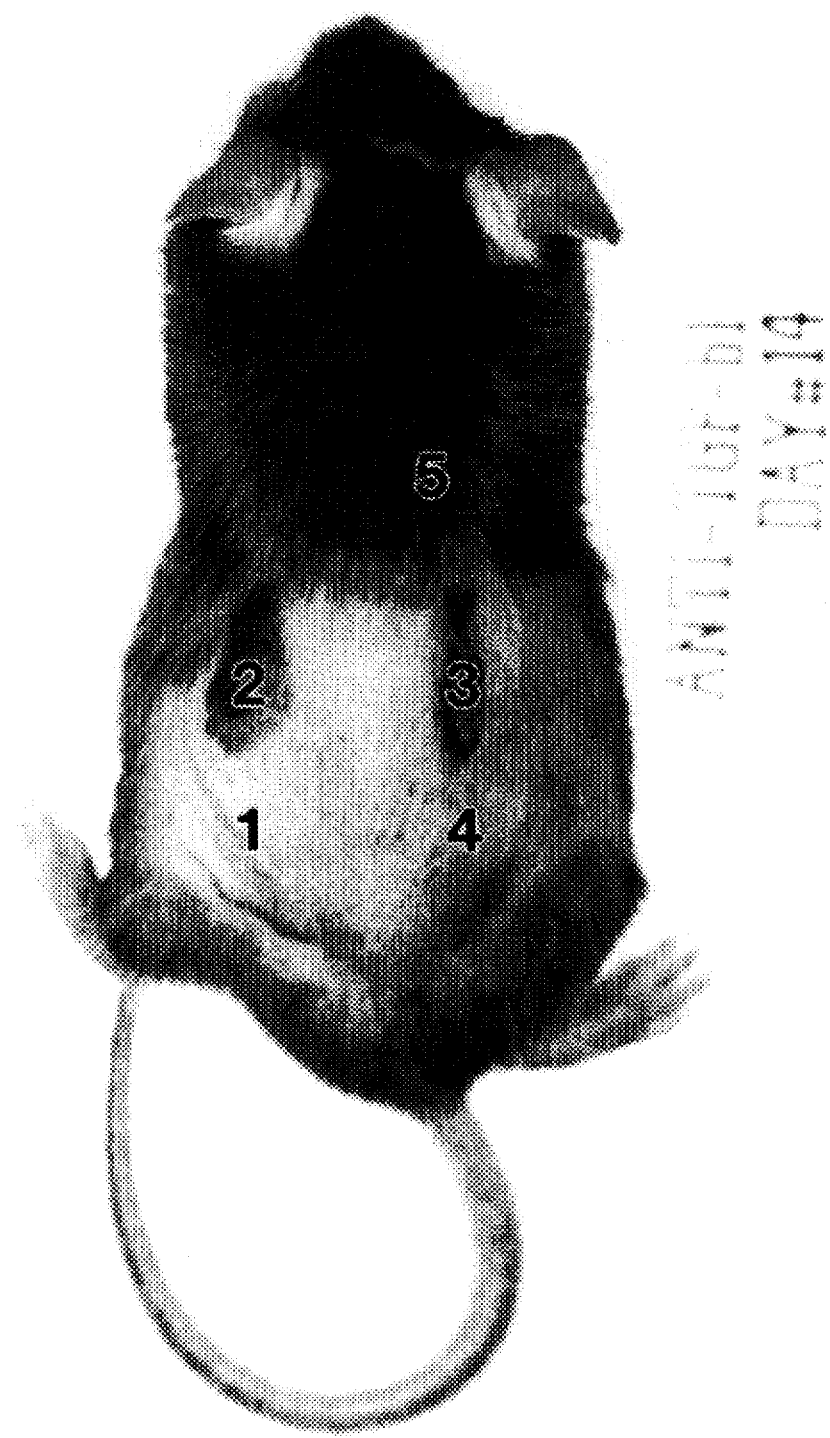
FIG. 14 is a photograph of the dorsal aspect of a C57BL/KsJ db/+ mouse taken 14 days post application of n-butyl cyanoacrylate, showing that new hair growth was present at sites 2 (which received topical n-butyl cyanoacrylate only) and 3 (which received topical n-butyl cyanoacrylate and subcutaneous PBS/0.1% BSA). There was a lack of hair growth at site 1 which received topical n-butyl cyanoacrylate and subcutaneous anti-TGF-β1 neutralizing antibody. This experiment suggests that TGF-β1 was a necessary part of the response to n-butyl cyanoacrylate.

Stimulation of hair growth at sites treated with n-butyl cyanoacrylate alone was clearly evident by day 14 at site 2 and 3 in Group B. In contrast, hair growth was much less at site 1 injected with anti-TGF-β1-neutralizing antibody (FIG. 14). After about 15–20 days post-treatment (i.e. at about 10–15 days after antibody injections were discontinued) hair at these sites attained the thickness of that at sites treated with n-butyl cyanoacrylate alone. Little effect was observed following injection of anti-EGF neutralizing antibody. These results implicate TGF-β1 in stimulation of hair growth following treatment with n-butyl cyanoacrylate.

C.9 Effect of Isobutyl Cyanoacrylate on Hair Growth

Figure 15:
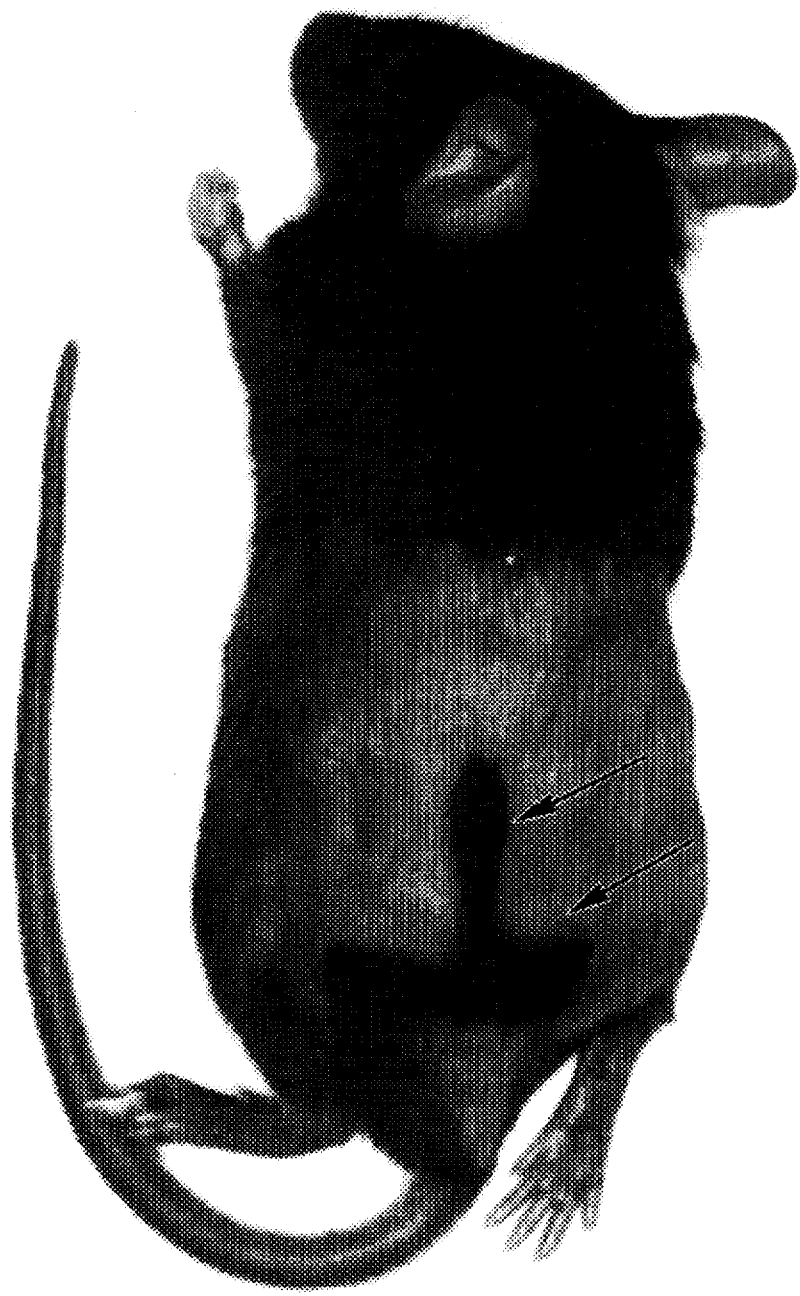
FIG. 15 is a photograph of the dorsal aspect of a C57BL/KsJ +/+ mouse taken 19 days post application of isobutyl cyanoacrylate, showing a "T" pattern of hair growth (arrows) in the treated area and the hairless skin in the shaved but untreated adjacent area.

The following experiment was performed to identify the effect of isobutyl cyanoacrylate, a structural analog of n-butyl cyanoacrylate, on hair growth. The shaved backs of C57BL/KsJ db/+ and C57BL/KsJ db/db mice were treated topically at a dose of 10 µl cm$^{-2}$ with either isobutyl cyanoacrylate (Sigma Chemical Co., St Louis, Mo.) or n-butyl cyanoacrylate. The hair growth response stimulated by isobutyl cyanoacrylate in both strains was nearly identical to that inducted by n-butyl cyanoacrylate: In treated area many new hair follicles occurred 2–3 days post treatment, hair growth was visible 8–12 days post treatment and reached full length at 15–18 days post treatment; the untreated areas were still hairless (FIG. 15 & Table 2), clearly demonstrating that the cyanoacrylate group in either n-butyl cyanoacrylate or isobutyl cyanoacrylate is the component responsible for hair growth.

TABLE 2

Effect of Cyanoacrylates on Hair Growth

| Agents | Species/strain | No. of animals | Hair growth* |
|---|---|---|---|
| IBC | C57BL/KsJ db/+ | 10 | 3+ |
|  | C57BL/KsJ db/db | 10 | 3+ |
| NBC | C57BL/KsJ +/+ | 10 | 3+ |
|  | C57BL/KsJ db/db | 10 | 3+ |

*The scoring scale used is: 0, no obvious hair growth; 1+, mild hair regeneration in an area defined as less than 10% of the treated area; 2+, moderate hair regeneration in an area larger than 10% but less than 50% of the treatred area; 3+, high hair regeneration with an area larger than 50% of the treated area. NBC, n-butyl cyanoacrylate; IBC, isobutyl cyanoacrylate.

C.10 Characteristics of Hair Growth Stimulated by Cyanoacrylate

Under this invention, two components in the family of cyanoacrylate, n-butyl cyanoacrylate and isobutyl cyanoacrylate, were tested in two species (rat and mouse) and seven strains of mouse (see section C.1) and found to stimulate hair growth in normal intact skin, in intact skin of the animals pre-treated with either of two anticancer drugs, and at the edges of excisional and incisional wounds.

The hair growth induced by n-butyl cyanoacrylate has the following characteristics:

1. A single application of the hair growth stimulator can induce hair follicle shift from telogen to anagen and de novo development of hair follicles, resulting in profound hair growth.

Figure 5A:
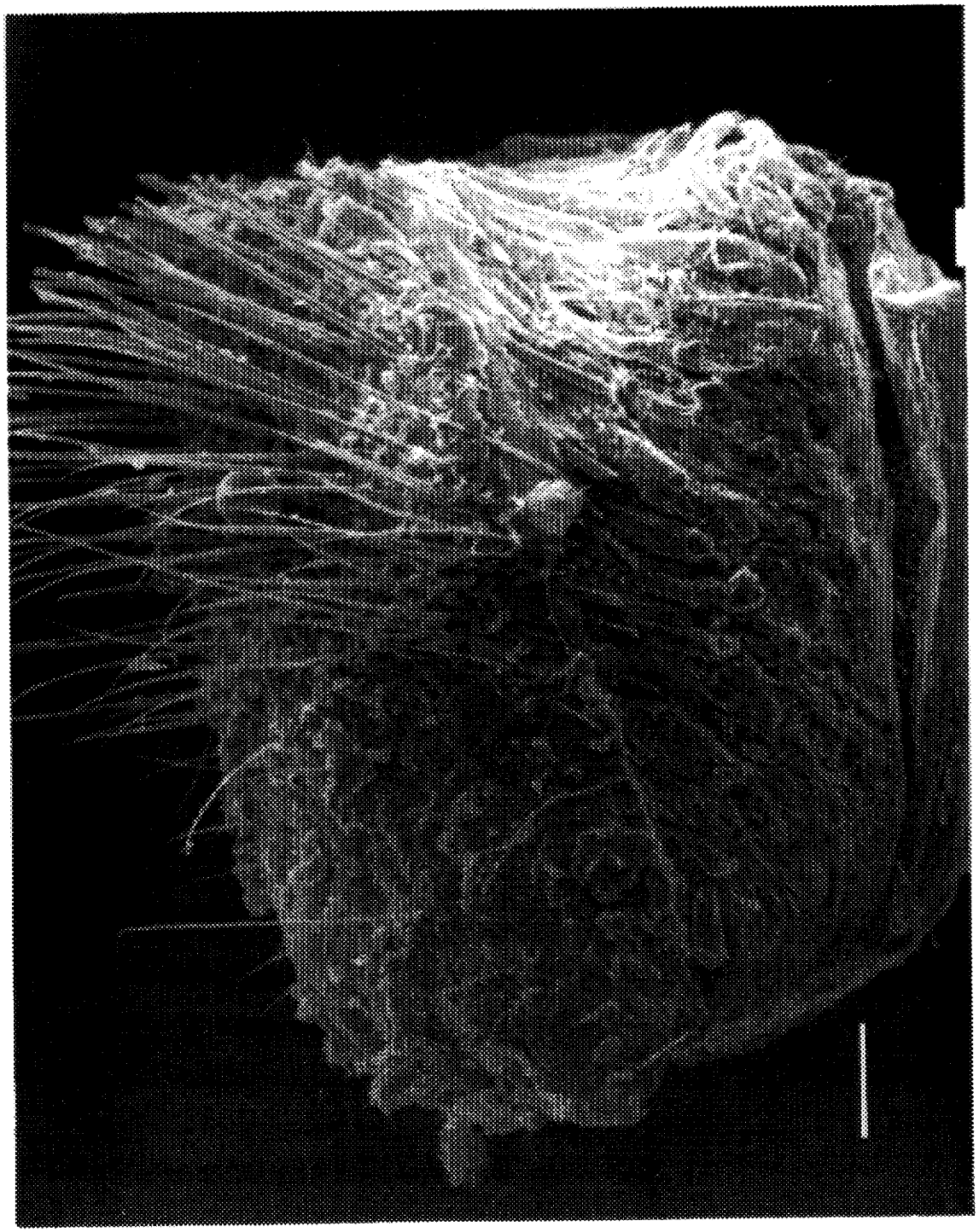
FIG. 5A is a scanning electron photomicrograph of a specimen of C57BL/KsJ db/+ mouse skin, showing a clear boundary between treated and untreated areas. At 23 days after n-butyl cyanoacrylate treatment, there is a higher density of hairs and deeper hair roots in the treated area (arrows) compared to the adjacent untreated area. The bar represents 200 μm.
Figure 5B:
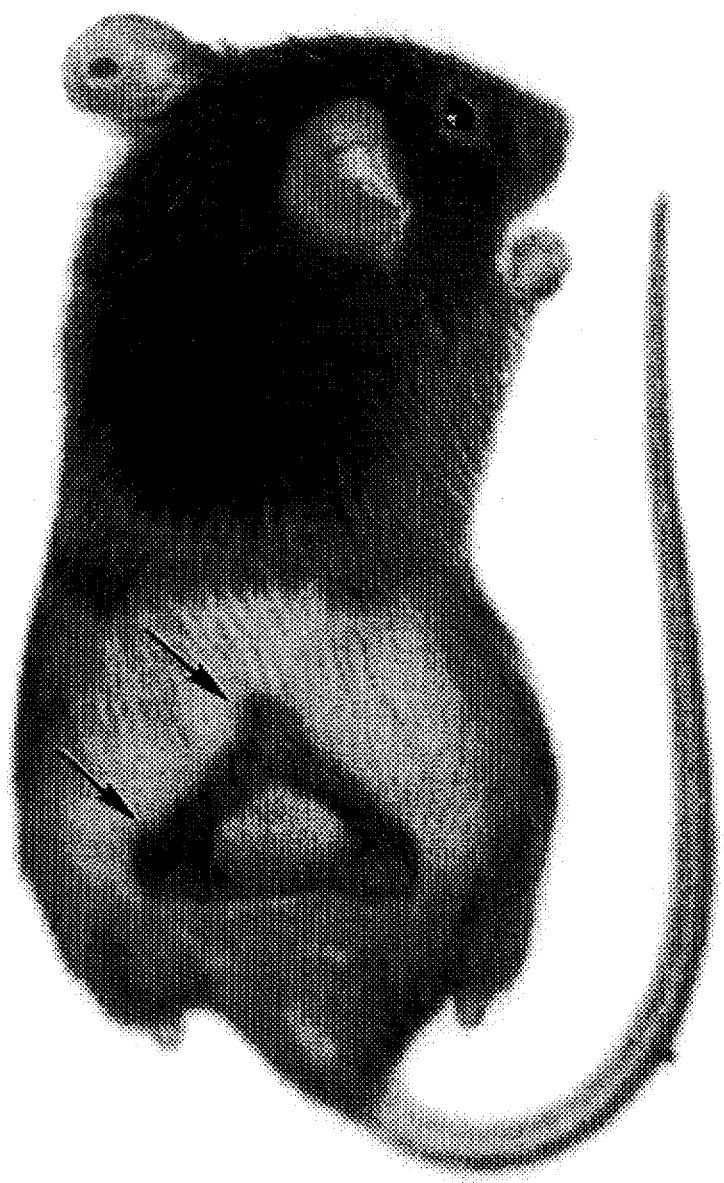
FIG. 5B is a photograph of the dorsal aspect of a C57BL/KsJ db/+ mouse taken 17 days post application of n-butyl cyanoacrylate, showing a triangle pattern of hair growth, which occurred exactly along the pattern of the application. The untreated adjacent skin remained hairless.

2. The reproducibility of hair growth induced by the stimulator at the dose of 10 mg/10 μl cm$^{-2}$ is 100% in more than 700 normal adult mice and rats, and 80 genetically healing-impaired diabetic (db/db) animals (FIGS. 5–7).

3. The ability of the stimulator to stimulate hair growth is very strong and specific. New hair follicle formation in the treated area occurs as early as 2–3 days after treatment (FIGS. 1A–1B); the skin thickened and the new hair growth can be seen as early as 8–12 days in treated area (FIGS. 2–3); the hair growth rate in the fastest growth period can reach 1 mm per day; and the size of new hair follicles is larger; and the new hairs are more pigmented, more coarse in diameter, and 1–2 mm longer than those in adjacent untreated area (FIGS. 5–8). Hair growth also can be induced ex vivo (FIG. 11), providing a useful model for studies on mechanisms of hair follicle formation and for tests of the effects of drugs on hair growth.

4. The hair growth can be induced even when the melanogenesis metabolism of hairs is severely suppressed by administration of an anticancer drug, cyclophosphamide (FIG. 10). Hair follicle regeneration and active pigment metabolism are closely related to each other and up to now there were no models in vitro or in vivo that could separate the two processes. Therefore, one advantage of this invention is to establish an experimental animal model to study the mechanism of melanogenesis.

5. The induced hair is the last pelage of the animals, and no shedding of hair has been found over 210 days in rats and 335 days in mice post treatment. Even in the genetically healing-impaired diabetic mice, hair regrowth in treated areas remains unchanged, but the shaved untreated areas are hairless more than 216 days post treatment. In contrast to this, after a single application of n-butyl cyanoacrylate, the hair keeps regrowing in the treated areas even if the area is subsequently shaved three times at 20-day intervals.

6. The induced hair growth is dose-dependent, i.e., the extent of hair growth varies with the extent of dilution and is adjustable. (Table 1).

7. The hair growth response is completely localized to the area where the stimulator is applied. A clear demarcation between treated and untreated skin signals the localized nature of the response. Scanning electron micrography revealed that hair follicles in treated skin were located deeper within the dermis than those in untreated skin (FIG. 5A).

8. No side effect or toxic effect or tumor-like tissue formation after the treatment has been observed except for a mild inflammation shortly after application.

EXAMPLES

Example 1

Induction of Hair Follicle Differentiation and Development in Adult Mammals

The dorsal aspect of C57BL/KsJ db/+ female mice was shaved and a single topical dose of n-butyl cyanoacrylate (formulated as Nexaband® Liquid) was applied. Beginning at day 2 post treatment, aggregates of cells formed in the adipose tissue of the subcutaneous layer. During subsequent days the number of such cellular aggregations increased. Only the outer cells stain positive for vimentin and are presumed to be of mesenchymal origin, consistent with the induction of hair follicles in treated skin by a mechanism similar to that occurring during the neo-natal period.

The observed development of hair follicles outside the dermis was confirmed above where n-butyl cyanoacrylate was applied to incisional and excisional wounds or injected subdermally.

Example 2

Stimulation of Hair Growth in a Domesticated Animal by Treatment with n-Butyl Cyanoacrylate A domesticated animal, for example, having undergone hair loss due to disease, cancer chemotherapy, aging, skin parasites, or other causes, is treated with a trichogenically effective formulation of a cyanocarboxylic acid derivative. Following treatment, new, normal terminal hair grows from the treated area. The treatment is repeated as necessary to provide hair growth at the desired level.

Example 3

Localized Induction of Hair Regrowth in Animals Following Injury

A domesticated animal, having undergone localized trauma to hair-bearing skin is mildly anesthetized, the wound dried, and 10 mg/cm$^2$ of n-butyl cyanoacrylate "painted" over the area of the wound. After a few seconds the n-butyl cyanoacrylate polymerizes and no other dressing is required. Within 10 days new hair grows from the healing or healed area.

Example 4

Cyanoacrylate Esters as Cosmetic Products for Show Animals

Esters of cyanoacrylate are effective as cosmetic products by providing show animals with increased quantity and improved quality of hair growth. Under the invention a physiologically effective formulation of a cyanoacrylate ester is applied topically to the skin of the subject animal, by brushing it to the underlying skin. Alternatively, the physiologically effective formulation may be applied to the coat and underlying skin by means of a spraying device or any other means known in the art. The dose and frequency of the application are varied depending on the nature of the animal and the type of results desired, as will be apparent to the skilled artisan. Following treatment, the coat grows thicker, is more pigmented and appears more healthy; as compared with the coat of a similar but untreated animal.

Example 5

Stimulation of Growth of the Coat of a Domesticated Animal Used as a Commercial Source of Fiber A physiologically effective amount of a suitable formulation of a cyanoacrylate ester is applied to an animal used as a commercial source of fiber. Application is effected as described in Example 4. Preferably treatment with cyanoacrylate ester occurs a suitable period of time prior to clipping the coat (e.g. in the case of sheep) or before sacrifice of the animal (e.g. mink). Suitable treatment of animals with an ester of cyanoacrylate improves both the quantity and quality of the fiber which they produce.

Example 6

Treatment of Skin of Domesticated Animals for Improved Leather & Suede Production Domesticated animals are treated with a physiologically effective amount of a formulation of an ester of cyanoacrylate, as described in Example 5. Due to the nature of the response of mammalian skin following treatment, only a single application may be required. Preferably the application is made a few days before slaughter. The optimum time for application depends on those considerations well within the grasp of those skilled in the art. This treatment provides superior leather products.

Example 7

Treatment of Alopecia in Humans with an Ester of Cyanoacrylate

A human patient with a hair loss problem is treated with a topical formulation comprising a trichogenically effective dose of an ester of cyanoacrylate which is applied to the affected area. The formulation is allowed to remain in situ for a period of about 24 hours. Such treatment results in stimulated hair growth within a period of a few days to a few weeks. The application may be repeated as necessary.

Example 8

Treatment of a Incisional or Excisional Wound on a Special Site in Humans

A human patient with a fresh incisional or excisional wound, or a pre-existed incisional or excisional wound on the scalp, the site(s) of mustache, eyebrow, beard, etc., is treated with a topical formulation comprising a trichogenically effective dose of an ester of cyanoacrylate which is applied to the affected area. Such treatment results in stimulated hair growth within a period of a few days to a few weeks, with an additional advantage that the normalizing process of the tissue (remodelling process) of the incisional or excisional wound is accelerated and scar formation is greatly decreased.

The present invention has been described in various embodiments, it will be apparent to one of ordinary skill that many modifications can be made thereto which nevertheless utilize the methods and compositions of the invention as disclosed. The scope of the invention is defined by the appended claims rather than by the embodiments presented above.

We claim:

1. A method for treating a mammal to induce or promote hair growth, hair follicle differentiation and development, melanogenesis, hair shaft elongation, skin cell differentiation or proliferation, or a shift in hair growth cycle from telogen to anagen comprising applying to a layer of viable skin of said mammal an effective amount of a pharmaceutically acceptable composition comprising a cyanocarboxylic acid derivative having the formula:

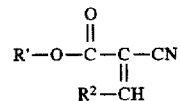

wherein $R^1$ is alkyl containing 1 to 20 carbons, cycloalkyl containing up to 20 carbons, alkenyl containing up to 20 carbons, alkynyl containing up to 20 carbons, aryl containing up to 20 carbons, alkaryl containing up to 20 carbons, aralkyl containing up to 20 carbons, or mono- or polyalkoxyalkyl containing up to 20 carbons; and $R^2$ is alkyl containing 1 to 10 carbons, cycloalkyl containing up to 10 carbons, alkenyl containing up to 10 carbons, alkoxyalkenyl containing up to 10 carbons, alkynyl containing up to 10 carbons, aryl containing up to 10 carbons, alkaryl containing up to 10 carbons, aralkyl containing up to 10 carbons, or H.

2. The method according to claim 1, wherein the cyanocarboxylic acid derivative has the formula:

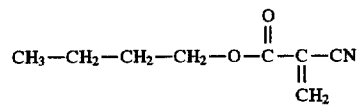

3. The method according to claim 1, wherein the cyanocarboxylic acid derivative has the formula:

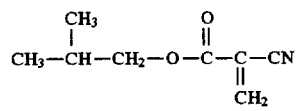

4. The method of claim 1, wherein an effective amount of the pharmaceutically acceptable composition is applied topically, intradermally, subcutaneously, or via dermal patch or slow-release mechanism to the layer of viable skin of the mammal.

5. The method of claim 4, wherein the mammal is a human.

6. The method of claim 4, wherein the mammal is a sheep.

7. The method of claim 4, wherein the pharmaceutically acceptable composition is applied in vitro to a layer of viable skin of the mammal.

8. The method according to claim 1, wherein the cyanocarboxylic acid derivative comprises from 0.0001 to 99% by weight of the pharmaceutically acceptable composition, and a pharmaceutically acceptable vehicle therefor.

9. The method of claim 8, wherein the cyanocarboxylic acid derivative comprises at least 25% by weight of the pharmaceutically acceptable composition.

10. The method of claim 8, wherein the cyanocarboxylic acid derivative comprises at least 50% by weight of the pharmaceutically acceptable composition.

11. A method according to claim 4, wherein the composition is applied to the skin by topical spray, shampoo, cream, ointment, salve, powder, sprayed powder, or the like.

12. The method of claim 1, wherein the composition is applied in vitro to a layer of viable skin of the mammal.

13. The method of claim 1, wherein the pharmaceutically acceptable composition is applied in vitro to a layer of viable skin of a mammal from which fur is to be obtained.

14. A method for treating a mammal to induce or promote hair growth, hair follicle differentiation and development, melanogenesis, hair shaft elongation, skin cell differentiation or proliferation, or a shift in hair growth cycle from telogen to anagen comprising applying to a layer of viable skin of said mammal an effective amount of a pharmaceutically acceptable composition comprising a cyanocarboxylic acid derivative having the formula:

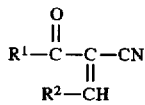

wherein $R^1$ forms an alkyl amide containing 1 to 20 carbons, an dialkyl amide containing up to 20 carbons, an alkoxyalkylamide containing up to 20 carbons, an anhydride containing up to 20 carbons, or an acyl halide containing up to 20 carbons, or $R^1$ is $NH_2$, and $R^2$ is alkyl containing 1 to 10 carbons, cycloalkyl containing up to 10 carbons, alkenyl containing up to 10 carbons, alkoxyalkenyl containing up to 10 carbons, alkynyl containing up to 10 carbons, aryl containing up to 10 carbons, alkaryl containing up to 10 carbons, aralkyl containing up to 10 carbons, or H, with the proviso that when $R^1$ is $NH_2$, $R^2$ is not aryl.

15. The method of claim 14, wherein an effective amount of the pharmaceutically acceptable composition is applied topically, intradermally, subcutaneously, or via dermal patch or slow-release mechanism to the layer of viable skin of the mammal.

16. The method of claim 15, wherein the mammal is a human.

17. The method of claim 15, wherein the mammal is a sheep.

18. The method of claim 15, wherein the pharmaceutically acceptable composition is applied in vitro to a layer of viable skin of the mammal.

19. The method according to claim 14, wherein the cyanocarboxylic acid derivative comprises from 0.0001 to 99% by weight of the pharmaceutically acceptable composition, and a pharmaceutically acceptable vehicle therefor.

20. The method of claim 19, wherein the cyanocarboxylic acid derivative comprises at least 25% by weight of the pharmaceutically acceptable composition.

21. The method of claim 19, wherein the cyanocarboxylic acid derivative comprises at least 50% by weight of the pharmaceutically acceptable composition.

22. A method according to claim 15, wherein the composition is applied to the skin by topical spray, shampoo, cream, ointment, salve, powder, sprayed powder, or the like.

23. The method of claim 14, wherein the composition is applied in vitro to a layer of viable skin of the mammal.

24. The method of claim 14, wherein the pharmaceutically acceptable composition is applied in vitro to a layer of viable skin of a mammal from which fur is to be obtained.

25. A method for treating a mammal to induce or promote hair growth, hair follicle differentiation and development, melanogenesis, hair shaft elongation, skin cell differentiation or proliferation, or a shift in hair growth cycle from telogen to anagen comprising applying to a layer of viable skin of said mammal an effective amount of a pharmaceutically acceptable composition comprising a cyanocarboxylic acid derivative selected from the group consisting of:

ethoxyethyl 2-cyanoacrylate,
butoxyethyl 2-cyanoacrylate,
n-butyl 2-cyanoacrylate,
isobutyl 2-cyanoacrylate,
n-propyl 2-cyanoacrylate,
isopropyl 2-cyanoacrylate,
n-hexyl 2-cyanoacrylate,
isohexyl 2-cyanoacrylate,
cyclohexyl 2-cyanoacrylate,
benzyl 2-cyanoacrylate,
glycerol 2-cyanoacrylate,
ethoxybutyl 2-cyanoacrylate,
n-pentyl 2-cyanoacrylate,
isopentyl 2-cyanoacrylate,
n-heptyl 2-cyanoacrylate,
isoheptyl 2-cyanoacrylate,
n-octyl 2-cyanoacrylate,
isooctyl 2-cyanoacrylate,
n-nonyl 2-cyanoacrylate,
isononyl 2-cyanoacrylate,
n-decyl 2-cyanoacrylate,
isodecyl 2-cyanoacrylate,
n-butyl 2-cyano-3-methoxyacrylate,
isobutyl 2-cyano-3-methoxyacrylate,
n-butyl 2-cyano-3-phenylacrylate,
isobutyl 2-cyano-3-phenylacrylate,
n-butyl 2-cyano-2-butenoate,
isobutyl 2-cyano-2-butenoate,
n-butyl 2-cyano-2-pentenoate,
isobutyl 2-cyano-2-pentenoate,
n-butyl 2-cyano-2-hexenoate,
isobutyl 2-cyano-2-hexenoate,
n-butyl 2-cyano-2-heptenoate,
isobutyl 2-cyano-2-heptenoate,
n-butyl 2-cyano-2-octenoate,
isobutyl 2-cyano-2-octenoate,
n-butyl 2-cyano-2-nonenoate,
isobutyl 2-cyano-2-nonenoate,
n-butyl 2-cyano-2-decenoate,
isobutyl 2-cyano-2-decenoate,
N-propyl 2-cyanoacrylamide,
N-butyl 2-cyanoacrylamide,
N-pentyl 2-cyanoacrylamide,
N-hexyl 2-cyanoacrylamide,
N-heptyl 2-cyanoacrylamide,
N-octyl 2-cyanoacrylamide,
N-nonyl 2-cyanoacrylamide, N-decyl 2-cyanoacrylamide,
N-benzyl 2-cyanoacrylamide,
N-cyclohexyl 2-cyanoacrylamide,
N-ethoxyethyl 2-cyanoacrylamide,
N-ethoxypropyl 2-cyanoacrylamide,
N-ethoxybutyl 2-cyanoacrylamide,
N-ethoxypentyl 2-cyanoacrylamide,
N-ethoxyhexyl 2-cyanoacrylamide,
N-ethoxyheptyl 2-cyanoacrylamide,
N-ethoxyoctyl 2-cyanoacrylamide,
N-ethoxynonyl 2-cyanoacrylamide,
N-ethoxydecyl 2-cyanoacrylamide,
N-propoxyethyl 2-cyanoacrylamide,
N-propoxypropyl 2-cyanoacrylamide,
N-propoxybutyl 2-cyanoacrylamide,
N-propoxypentyl 2-cyanoacrylamide,
N-propoxyhexyl 2-cyanoacrylamide,
N-propoxyheptyl 2-cyanoacrylamide,
N-propoxyoctyl 2-cyanoacrylamide,
N-propoxynonyl 2-cyanoacrylamide,
N-propoxydecyl 2-cyanoacrylamide,
N-butoxyethyl 2-cyanoacrylamide,
N-butoxypropyl 2-cyanoacrylamide,
N-butoxybutyl 2-cyanoacrylamide,
N-butoxypentyl 2-cyanoacrylamide,
N-butoxyhexyl 2-cyanoacrylamide,
N-butoxyheptyl 2-cyanoacrylamide,
N-butoxyoctyl 2-cyanoacrylamide,
N-butoxynonyl 2-cyanoacrylamide, and
N-butoxydecyl 2-cyanoacrylamide.

* * * * *